United States Patent [19]

Saito et al.

[11] Patent Number: 5,041,447
[45] Date of Patent: Aug. 20, 1991

[54] OXETANOCIN-RELATED COMPOUNDS AND PHARMACEUTICAL COMPOSITIONS CONTAINING THEM

[75] Inventors: Seiichi Saito, Kashiwa; Shigeru Hasegawa, Yono; Katsutoshi Takahashi; Nobuyoshi Shimada, both of Tokyo; Jun-ichi Seki, Takasaki; Hiroo Hoshino, Maebashi; Yukihiro Nishiyama, Aichi; Kenichi Matsubara, Suita; Takemitsu Nagahata, Toyonaka, all of Japan

[73] Assignee: Nippon Kayaku Kabushiki Kaisha, Tokyo, Japan

[21] Appl. No.: 325,230

[22] Filed: Mar. 17, 1989

[30] Foreign Application Priority Data

Mar. 23, 1988 [JP] Japan .................................. 63-67253
Sep. 20, 1988 [JP] Japan ................................. 63-233650

[51] Int. Cl.$^5$ .................... A61K 31/52; C07D 473/34; C07D 473/18; C07D 473/30
[52] U.S. Cl. .................................... 514/262; 514/265; 514/266; 544/265; 544/267; 544/276; 544/277
[58] Field of Search ........................ 544/276, 277, 265; 514/265, 266

[56] References Cited

U.S. PATENT DOCUMENTS 4,743,689  5/1988  Shimada et al. ..................... 544/277
4,845,215  7/1989  Shimada et al. ..................... 544/265

FOREIGN PATENT DOCUMENTS 0182315 11/1985  European Pat. Off. .
0291917 11/1988  European Pat. Off. ............ 544/267
0208295  9/1987  Japan .
0303993 12/1988  Japan .................................. 544/264

OTHER PUBLICATIONS

J. of Antibiotics, vol. 39(11), pp. 1623–1625, Shimada et al.
Niitsuma et al., Tetrahedron Letters, vol. 28(34), pp. 3967–3970 (08/87).
Hoshino et al., J. Antibiot., vol. 40(7), pp. 1077–1078 (07/87).
Shimada et al., J. Antibiot., vol. 40(12), pp. 1788–1780 (12/87).
Niitsuma et al., Chemical Abstracts, vol. 109: 38158q (1988).
Norbeck et al., J. Am. Chem. Soc., vol. 110(21), pp. 7217–7218 (10/88).

*Primary Examiner*—Diana Rivers
*Attorney, Agent, or Firm*—Henry C. Nields

[57] ABSTRACT

This invention relates to oxetanocin-related compounds represented by the following formula (I):

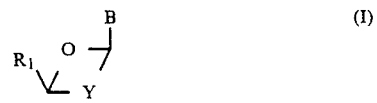

[in formula (I), $R_1$, Y and B have the following meanings:
(a) $R_1$ represents —$CH_2OH$ or —$CH_2OCO$-(alkyl),
(b) Y represents

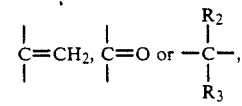

provided that $R_2$ is —H, —OH or —$CH_2OH$ and $R_3$ is —H, —OH, halogen atom, —$CH_2OH$, lower alkyl group, —$CH_2$-$N_3$, —$CH_2$-F, —$N_3$, —COOH, —$NH_2$, —$CH_2OSO_3H$ or —$CH_2OCO$-(lower alkyl), and
(c) B represents a residue of purine base,
(d) provided that $R_1$ and $R_3$ cannot simultaneously represents —$CH_2OH$]

and their salts which have activities such as an antiviral activity and the like and are expectedly useful as a pharmaceutical and the like.

8 Claims, No Drawings

OXETANOCIN-RELATED COMPOUNDS AND PHARMACEUTICAL COMPOSITIONS CONTAINING THEM

BACKGROUND OF THE INVENTION

1. Field of the Invention

This invention relates to novel oxetanocin-related compounds and salts thereof. More particularly, this invention relates to oxetanocin-related compounds and salts thereof having activities such as antiviral activity and the like and being expectedly useful as medicine and the like.

2. Description of the Prior Art

Oxetanocin itself is well known, because it is disclosed in Journal of Antibiotics, Vol. 39, No. 11, Pages 1623-25 (1986), EP-A2-0182312, etc.

Its derivatives are also disclosed in Journal of Antibiotics, Vol. 40, No. 12, Pages 1788-90 (1987).

At the present time, no satisfactory therapeutic drug is available for viral diseases. Thus, it is desired to develop an antiviral agent.

SUMMARY OF THE INVENTION

This invention relates to oxetanocin-related compounds represented by the following general formula

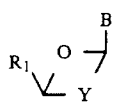
(I)

wherein $R_1$, Y and B have the following meanings:
(a) $R_1$ represents $-CH_2OH$ or $-CH_2OCO-(alkyl)$,
(b) Y represents

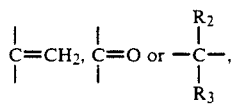

provided that $R_2$ represents $-H$, $-OH$ or $-CH_2OH$ and $R_3$ represents $-H$, $-OH$, halogen atom, $-CH_2OH$, lower alkyl group which may be substituted by halogen atoms, $-CH_2-N_3$, $-N_3$, $-COOH$, $-NH_2$, $-CH_2OSO_3H$ or $-CH_2OCO-(lower\ alkyl)$,
(c) B represents a purine base residue,
(d) provided that $R_1$ and $R_3$ cannot simultaneously represents $-CH_2OH$,
as well as to salts of said oxetanocin-related compounds and a process for producing them.

The oxetanocin-related compounds of this invention exhibit an antiviral action and the like and are expectedly useful as a therapeutic drug for various viral diseases.

DETAILED DESCRIPTION OF THE INVENTION

In view of the above-mentioned present status of things, the present inventors conducted many studies to find that oxetanocin-related compounds represented by the following general formula (I):

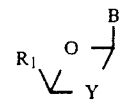
(I)

wherein $R_1$, Y and B have the following meanings:
(a) $R_1$ represents $-CH_2OH$ or $-CH_2OCO-(alkyl)$,
(b) Y represents

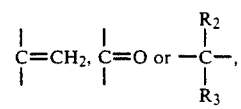

provided that $R_2$ represents $-H$, $-OH$ or $-CH_2OH$ and $R_3$ represents $-H$, $-OH$, halogen atom, $-CH_2OH$, lower alkyl group which may be substituted by halogen atoms, $-CH_2-N_3$, $-N_3$, $-COOH$, $-NH_2$, $-CH_2OSO_3H$ or $-CH_2OCO-(lower\ alkyl)$,
(c) B represents a purine base residue,
(d) provided that $R_1$ and $R_3$ cannot simultaneously represente $-CH_2OH$,
and salts of said oxetanocin-related compounds have an antiviral action. Based on the finding, this invention was accomplished.

Typical examples of the alkyl group usable in the invention include alkyl groups such as methyl, ethyl, propyl, butyl, pentyl, hexyl, heptyl, octyl, nonyl, decyl, undecyl, dodecyl, tetradecyl, pentadecyl, heptadecyl, octadecyl, eicosyl and the like. These alkyl groups may be any of straight chain type and branched chain type, and may contain a substituent, if desired.

As the lower alkyl group used herein, alkyl groups having about 1 to 6 carbon atoms can be referred to. The lower alkyl group may be any of straight chain type and branched chain type. Lower alkyl groups substituted by halogen atom (for example, fluorine atom, bromine atom, chlorine atom) and the like are also included in said lower alkyl group.

As the purine base residue, residues of purine derivatives linked to an oxetane ring at the 9-position of purine skeleton represented by the following formula:

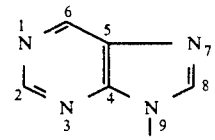

can be referred to. Examples of the purine base residue include adenine residue, guanine residue, xanthine residue, hypoxanthine residue, 2,6-diaminopurine residue, and the like.

Concrete examples of the compound of general formula (I) are listed in Table 1.

In Table 1 and the formulas shown below, the meanings of the abbreviations are as follows:

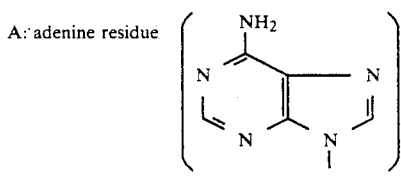

A: adenine residue

G: guanidine residue 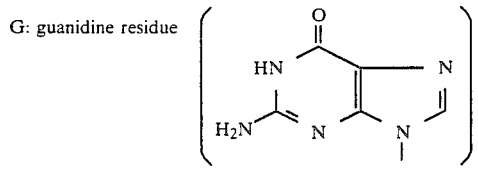

H: hyproxanthine residue 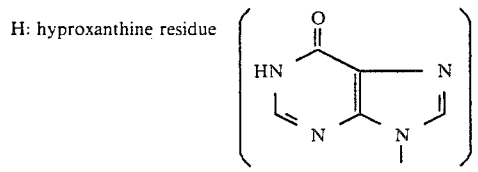

X: xanthine residue 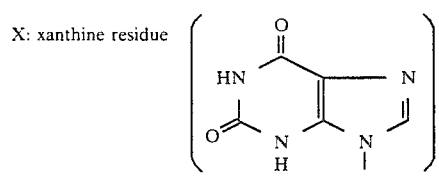

D: 2,6-diaminopurine residue 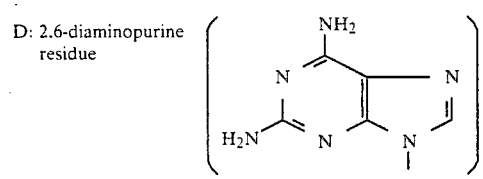

TABLE 1

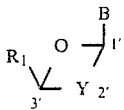

(I)

| Compound No. | B | Y | $R_1$ |
|---|---|---|---|
| 1 | A | $-CH_2$ | $HO-CH_2-$ |
| 2 | " | $-CH(CH_2-N_3)-$ | " |
| 3 | " | $-CH(OH)-$ | " |
| 4 | " | $-C(=CH_2)-$ | " |
| 5 | " | $-CH(CH_2F)-$ | " |
| 6 | " | $-CH(CH_3)-$ | " |
| 7 | " | $-C(CH_2OH)(OH)H-$ | " |
| 8 | A | $-CH(CH_2-OH)-$ | $CH_3(CH_2)_3C(=O)-O-CH_2-$ |
| 9 | " | $-CH(CH_2-OH)-$ | $CH_3(CH_2)_{14}C(=O)-O-CH_2-$ |
| 10 | " | $-CH(F)-$ | $HO-CH_2-$ |
| 11 | " | $-CH(N_3)-$ | " |
| 12 | H | $-CH(OH)-$ | " |
| 13 | H | $-CH_2-$ | " |
| 14 | G | $-CH(CH_2OH)-$ | $CH_3(CH_2)_3C(=O)-O-CH_2-$ |
| 15 | D | $-CH(CH_2OH)-$ | $CH_3(CH_2)_3C(=O)-O-CH_2-$ |
| 16 | A | $-CH(NH_2)-$ | $HO-CH_2-$ |
| 17 | H | $-CH(CH_2OSO_3Na)-$ | $HO-CH_2-$ |
| 18 | H | $-CH(CH_2OCOCH_2CH_3)-$ | $HO-CH_2-$ |

TABLE 1-continued

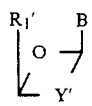

(I)

| Compound No. | B | Y | $R_1$ |
|---|---|---|---|
| 19 | H | −CH(CH$_2$OCOCH$_3$)/ | HO−CH$_2$− |
| 20 | A | −CH(COOH)/ | HO−CH$_2$− |

The compound of this invention is produced by eliminating the protecting group from a protected oxetanocin-related compound represented by the following formula (I-a):

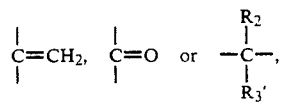

(I-a)

[ in the formula, $R_1'$, $Y'$ and B have the following meanings:
(a) $R_1'$ represents $-CH_2O-P_1$ ($P_1$ is protecting group) or $R_1$, provided that $R_1$ represents $-CH_2OH$ or $-CH_2OCO-$(alkyl);
(b) $Y'$ represents $-CH_2O-P_1$ ($P_1$ is protecting group) or $Y$, provided that $Y$ represents $$\overset{|}{\underset{|}{C}}=CH_2, \quad \overset{|}{\underset{|}{C}}=O \quad \text{or} \quad -\overset{R_2}{\underset{R_3'}{\overset{|}{C}}}-,$$

wherein $R_2$ is $-H$, $-OH$ or $-CH_2OH$, $R_3'$ is $-CH_2O-P_1$ ($P_1$ is protecting group) or $R_3$, and $R_3$ is $-H$, $-OH$, halogen atom, $-CH_2OH$, lower alkyl group which may be substituted by halogen atoms, $-CH_2-N_3$, $-N_3$, $-COOH$, $-NH_2$, $-CH_2OSO_3H$ or $-CH_2OCO-$(lower alkyl);
(c) B represents a residue of purine base of which functional group may optionally be protected;
(d) provided that $R_1'$ and $R_3'$ cannot simultaneously represent $-CH_2OH$ nor $-CH_2O-P_1$, and at least one of $R_1'$, $R_3'$ and B must have a protecting group] or its salt to form an oxetanocin-related compound represented by the following formula (I):

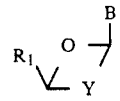

(I)

[in formula (I), $R_1$ and Y are as defined above and B represents a purine base] or its salt.

For example, a compound represented by the following general formula (I'):

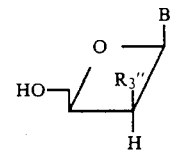

(I')

wherein B is as defined above and $R_3''$ represents $-H$ or $-OH$, which is one of the typical examples of the oxetanocin-related compound of this invention, can be synthesized by eliminating the protecting group from a protected oxetanocin-related compound represented by the following general formula (II):

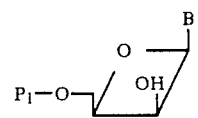

(II)

wherein $P_1$ and B are as defined above, or by dehydroxylating the protected oxetanocin-related compound and thereafter eliminating the protecting group.

The protected oxetanocin-related compound represented by general formula (II) can be obtained by converting the sugar part of Oxetanocin A, Oxetanocin H, Oxetanocin X, Oxetanocin G or 2-amino-Oxetanocin A [Journal of Antibiotics, Vol. 40, No. 12, Pages 1788-90 (1987)] by a chemical method.

Next, production process of a typical compound of general formula (I) wherein B is adenine residue (A) will be briefly mentioned below. In the formulas,

represents a group represented by the following formula:

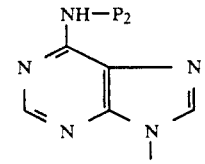

wherein $P_2$ represents a protecting group.

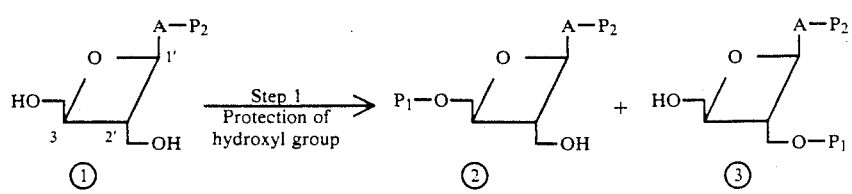

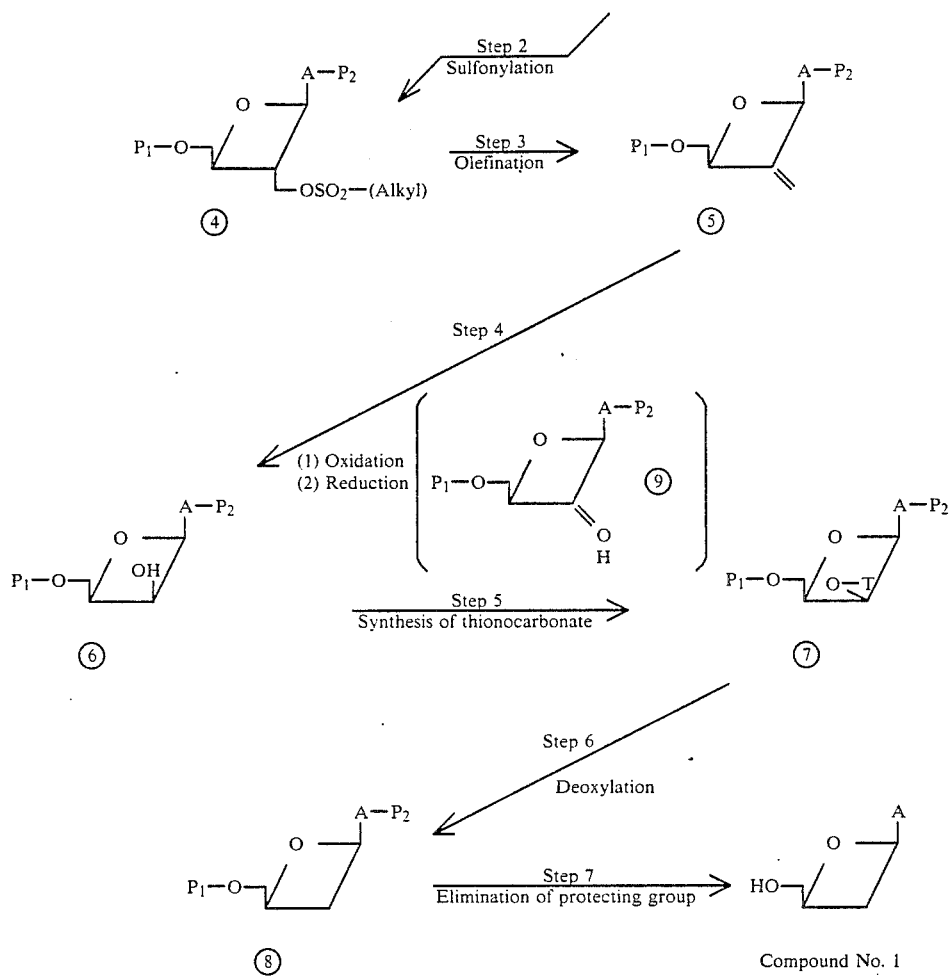

In the above-mentioned formulas, $P_1$ is as defined above and T represents thionocarbonate group.

Each of the steps mentioned above will be explained below.

Step 1: The hydroxyl groups in 2'—$CH_2OH$ and 3'—$CH_2OH$ of N(6)-protected oxetanocin ① are selectively protected with some protecting group.

As the protecting group ($P_1$ and $P_2$) of compounds ② and ③, formyl group, (lower alkyl)-carbonyl groups optionally substituted by halogen atom, lower alkoxy group, benzoyl group or the like (for example, acetyl, chloroacetyl, trichloroacetyl, methoxyacetyl, pivalotyl, phenoxyacetyl, trityloxyacetyl and the like), acyl groups (for example, benzoyl and the like) and optionally substituted lower alkyl groups including unsubstituted lower alkyl groups such as t-butyl and the like and substituted lower alkyl groups such as unsubstituted trityl and substituted trityls [for example, (lower alkoxy)-trityls such as monomethoxytrityl, dimethoxytrityl, trimethoxytrityl and the like] can be referred to.

Further, silyl type protecting groups, i.e. silyl groups having various substituents (for example, trimethylsilyl, t-butyldimethylsilyl, t-butyldiphenylsilyl and the like) can also be referred to.

The above-mentioned protecting group can be introduced according to hitherto known methods. Preferably, a protecting group which can be eliminated effectively afterwards is selected. Compound ② and compound ③ can be separated from each other by column chromatography.

Step 2: This is a step for sulfonylating the hydroxyl group of 2'—$CH_2OH$ of compound ②. Examples of the sulfonylating agent used for this purpose include alkyl- and aryl-sulfonyl halogenides such as methanesulfonyl chloride, p-toluenesulfonyl chloride, 2,4,6-triisopropylbenzenesulfonyl chloride and the like.

Step 3: This is a step for forming an olefin by treating compound ④ with a base. As the base, alkali metal lower alcholates such as t-butoxypotassium and the like are preferably used.

Step 4: In this step, the olefin compound ⑤ is oxidized (Lemieux-von Rudloff oxidation) with potassium permanganate or sodium periodate to form a ketone compound and then reducing the latter with a metal hydride to form a secondary hydroxyl group (Compound ⑥). Examples of the metal hydride usable for this purpose include sodium boron hydride, sodium trimethoxyboron hydride, sodium boron hydride cyanide, lithium triethoxyaluminum hydride, lithium aluminum hydride and the like.

Step 5: This is a step for converting the resulting secondary alcohol to a thionocarbonate. As an agent for producing thionocarbonate, phenyl chlorocarbonothionate can be used.

Step 6: In this step, compound ⑦ is treated with tributyltin hydride and α,α'-azobis-isobutyronitrile to eliminate the thionocarbonate part.

Step 7: This is a step for eliminating the protecting groups $P_1$ and $P_2$. For this purpose, a basic compound exercising no substantial influence upon the oxetane ring is used. Its amount may be any amount, so far as the amount adopted is enough to cause a substantial elimination of the protecting groups. Preferably, it is used in at least an amount theoretically equivalent to the protected oxetanocin-related compound. As the reaction temperature, a temperature not exceeding the boiling point of the used solvent (for example, about $-40°$ C. to about 150° C.) can be adopted. Usually, the reaction is carried out at a temperature of 0° C. to 100° C. When the protecting group $P_1$ is a silyl type protecting group (silyl group having various substituents), an ammonium compound such as tetra-n-butylammonium fluoride can be used in tetrahydrofuran, for example.

When $P_2$ is an acyl group, an alkali metal alkoxide such as sodium methoxide, ammonia water, and the like can be used.

A compound of general formula (I) wherein B is adenine residue (A) and Y is $$-\overset{O}{\underset{\|}{C}}-$$

can be produced by oxidizing compound  to form a compound represented by the following formula :

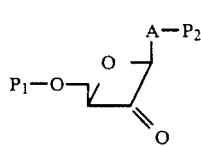 (9)

and then eliminating the protecting groups therefrom.

A compound of general formula (I) wherein B is adenine residue (A) and Y is $$-\overset{CH_2}{\underset{\|}{C}}-$$

(compound No. 4) can be obtained by eliminating the protecting groups from compound .

Further, compound No. 3 can be obtained by eliminating the protecting groups from compound , and compounds wherein Y is $$-\underset{CH_2-(halogen)}{\overset{H}{\underset{|}{C}}}-$$

such as compound No. 5 can be obtained by halogenating compound  and then eliminating the protecting groups.

A compound of formula (I) wherein B is adenine residue (A) and $R_1$ is $-CH_2OCO-(alkyl)$ can be obtained by acylating a compound of the following formula ′:

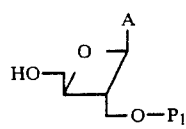 (3)′ in the usual manner and then eliminating the protecting group $P_1$. The protecting group $P_1$ must be capable of elimination under a condition not affecting the acyl group. A prefereable protecting group $P_1$ is silyl group, for example.

When B is a residue of other bases such as guanine residue (G), hypoxanthine residue (H), xanthine residue (X) or 2,6-diaminopurine residue, the intended compounds can be obtained similarly by treating the corresponding compounds according to the above-mentioned procedure.

Compounds of formula (I) wherein B is hyposanthine base can be obtained not only by the above-mentioned method but also by a method mentioned below.

Thus, an oxetanocin-A (OXT-A) related compound represented by the following formula (I-b):

 (I-b)

wherein A is adenine residue and $R_1$ and Y are as defined above, is treated with adenosine deaminase to form an oxetanocin-H (OXT-H) related compound represented by the following formula (I-c):

 (I-c)

wherein H is hypoxanthine residue and $R_1$ and Y are as defined above.

The temperature at which OXT-A is treated with adenosine deaminase is not critical, so far as the enzyme can act. However, it is usually about 10° C. to about 50° C., and preferably about 15° C. to about 40° C.

The solvent used in this reaction is not critical, so far as it does not disturb the action of the enzyme. Usually, however, aqueous solvents such as water and the like are used. Preferably, the reaction is carried out in the neighborhood of neutral pH by the use of a buffer solution.

It is also possible to obtain a compound of formula (I) wherein Y is

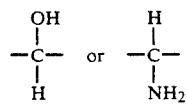

by reducing the corresponding ketone or azide compound, respectively.

Thus, an oxetanocin-related compound represented by the following formula (I-e):

 (I-e)

wherein $R_1'$ represents $-CH_2OH$ or $-CH_2O-P_1$ ($P_1$ is protecting group), B represents a residue of purine base of which functional group may optionally be protected, and Y″ represents

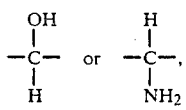

or its salt can be obtained by reducing an oxetanocin-related compound represented by the following formula (I-d):

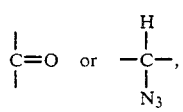 (I-d)

wherein $R_1'$ and B are as defined above and Y' represents

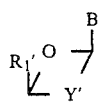

or its salt in an inert solvent by a catalytic reduction using Pd/black or by a reduction using a boron hydride compound such as alkali metal boron hydride. The inert solvents used in the catalytic reduction are for example water, an acetic acid and a lower alcohol such as methanol or ethanol and that used in the reduction by a boron hydride compound is acetonitrile, tetrahydrofuran or a lower alcohol. The reaction temperature may be a conventional temperature. For example, the reaction can be carried out in the temperature range from about 0° C. to the boiling point of the solvent, and preferably from about 5° C. to about 80° C.

The catalytic reduction is usually used, to obtain the compound of

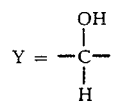

from the compound of

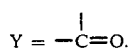

The reduction using a boron hydride compound is usually used to obtain the compound of

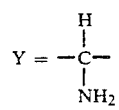

ps from the compound of

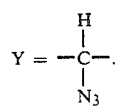

Further, since the compounds of this invention exhibit an antiviral activity against DNA virus or(and) RNA virus and the like, they are expectedly usable as an antiviral agent. Examples of the viruses controllable with the compounds of this invention include retrovirus including human immunodeficiency virus, Adenovirus, Parvovirus, Papovavirus, Poxvirus, Herpesvirus, Cytomegalovirus, hepatitis B virus, Togavirus, Arenavirus, and the like.

Compounds of this invention wherein $R_1$ is —CH$_2$OH or —CH$_2$OCO—(alkyl), Y is

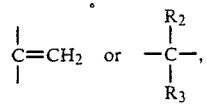

$R_2$ is —H or —OH, and $R_3$ is —H, halogen atom, —CH$_2$OH, —CH$_2$—N$_3$, —CH$_2$—F or —N$_3$ are preferable, because they have an intense antiviral activity.

Among these compounds, those wherein B is adenine base residue (A) or hypoxanthine base residue (H), $R_1$ is —CH$_2$OH, Y is

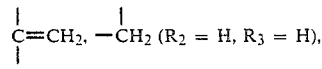

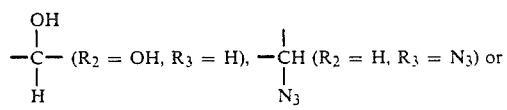

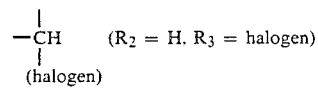

and their salts exhibit an intense activity against HIV virus with a low toxicity such as cytoxicity and the like.

Compounds wherein B is guanine base residue (G) or 2,6-diaminopurine base residue (D), $R_1$ is —CH$_2$OCO—(alkyl) and Y is

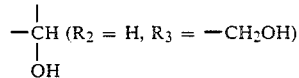

are preferable, because they exhibit an excellent activity against B hepatitis virus, Cytomegalovirus, Herpes-simplex and the like probably with only a low toxicity and without carcinogenicity.

Next, test examples and examples of this invention will be illustrated below.

TEST EXAMPLE

Anti-HIV (human immunodeficiency virus) activity

MT-4 cell (about 100,000 cells/ml) was added into a 24 well tray, and then 100 microliters of a solution containing a predetermined quantity of a compound of this invention was added. After culturing it at 37° C. for 5 hours in 5% (v/v) carbon dioxide incubator, $10^3$ to $10^4$ infection units of HIV was added and cultured for 4 days. Then, a part of the cultured fluid was coated onto a slide glass and immobilized with acetone, after which development of virus antigen was observed by indirect fluorescent antibody method.

As the primary antibody of the fluorescent antibody method, a serum of AIDS patient was used. As its secondary antibody, FITC-labelled human IgG was used.

Cell denaturation of MT-4 cells by the compound of this invention was carried out without adding virus, and it was visually examined under microscope.

TABLE 2

Anti-HIV activities of the compounds of this invention

| Compound No. | Concentration (μg/ml) | Cell denaturation | Development of virus antigen (%) |
| --- | --- | --- | --- |
| 1 | 100 | ++ | <0.1 |
|   | 10 | ± | <0.1 |
|   | 3 | − | 0.1 |
| 2 | 100 | ± | <0.1 |
|   | 10 | − | 10 |
|   | 3 | − | 15 |
| 3 | 100 | ± | <0.1 |
|   | 10 | − | 0.1 |
|   | 3 | − | 1 |
| 4 | 100 | ± | <0.1 |
|   | 10 | − | 3 |
|   | 3 | − | 10 |
| 8 | 100 | ++ | <0.1 |
|   | 10 | ± | 3 |
|   | 3 | − | 5 |
| 9 | 100 | +++ | <0.1 |
|   | 10 | + | 3 |
|   | 3 | ± | 7 |
| 10 | 100 | + | <0.1 |
|   | 10 | − | 50 |
|   | 3 | − | >90 |
| 11 | 100 | ± | <0.1 |
|   | 10 | − | 75 |
|   | 3 | − | >90 |
| 13 | 100 | + | <0.1 |
|   | 10 | − | <0.1 |
|   | 3 | − | <0.1 |
| 16 | 100 | ± | <0.1 |
|   | 10 | − | 6 |
|   | 3 | − | 17 |
| 17 | 100 | ± | <0.1 |
|   | 10 | − | 10 |
|   | 3 | − | 60 |

Note:
The compounds of this invention were used in the form of a solution in dimethylsulfoxide (DMSO). In a run using DMSO only, the development of virus antigen was 80 to 90%.

Anti-cytomegalovirus activity

Anti-cytomegalovirus activity was determined in the following manner. Thus, a 35 mmφ dish containing a single layer of human fetal fibroblasts was infected with 100 PFU (plaque forming units) of cytomegalovirus (A0169 strain). After adsorption for one hour, a medium (0.5% agarose, 2% fetal calf serum) containing a varied concentration of the compound of this invention was superposed thereon, and the whole was cultured at 37° C. for 10 days in 5% (v/v) carbon dioxide incubator, after which the formation of plaque was measured. The results are shown in Table 3 in terms of 50% inhibitory value ($IC_{50}$).

TABLE 3

| Compound No. | Anti-cytomegalovirus activity $IC_{50}$ (μg/ml) |
| --- | --- |
| 9 | 1.7 |
| 14 | >5 |
| 15 | >5 |

(d) Hepatitis B virus inhibitory activity

According to Dulbecco, a cultured liver cell strain HB 611 producing and releasing active hepatitis B virus [Proc. Natl. Acad. Sci. USA, 84 (1987), p. 444] was cultured at 37° C. in modified Eagle medium (GIBCO) in the presence of 10% fetal calf serum, 200 micrograms/ml of G418, 100 u/ml of Penicillin and 100 u/ml of Streptomycin with 5% carbon dioxide. It was inoculated into 6-well plate at a rate of $5 \times 10^4$ cells/well (35 mmφ). When 50% confluent was reached in one or two days, a predetermined quantity of the compound of this invention was added and the culture was continued. Thereafter, the medium was exchanged with a fresh medium containing the same test chemical at the same concentration at intervals of every 3 days, and the culture was continued for 15 days in the total. Then, the medium was removed, and the cell was treated with 0.5 ml of lysis buffer (10 mM Tris-HCl, pH 7.8/5 mM $Na_2EDTA$, 1% SDS/0.1 mg/ml Pronase K) at 37° C. for one hour to obtain a solution. The DNA thus obtained was purified by RNase treatment, phenol-chloroform treatment, and ethanol precipitation method. Then, 5 micrograms of DNA was subjected to Hind III treatment, and DNA pattern was analyzed by southern blot method by using $^{32}P$-labelled hepatitis B virus DNA as a probe. The results are shown in Table 4.

TABLE 4

Anti-hepatitis B virus activity of the compounds of this invention

| Compound No. | Concentration (μg/ml) | Virus DNA synthesis inhibitory effect | Cytotoxicity |
| --- | --- | --- | --- |
| 3 | 50 | +++ | ++ |
|   | 10 | ++ | − |
|   | 2 | + | − |
| 4 | 50 | n.t | ++ |
|   | 10 | ++ | − |
|   | 2 | + | − |
| 14 | 10 | ++ | − |
|   | 1.0 | + | − |
|   | 0.1 | ± | − |
| 15 | 10 | ++ | − |
|   | 1.0 | + | − |
|   | 0.1 | ± | − |
| Control | 0 | − | − |

As is apparent from the table shown above, the compound of this invention exhibits a remarkable growth-inhibitory activity on HIV with only a small extent of cell denaturation. Accordingly, the compounds of this invention are expected to be effectively usable as a therapeutic drug for AIDS.

Next, synthesis and properties of the compounds of this invention will be mentioned concretely by way of the following examples.

Among the abbreviations signifying the characteristics of the compounds obtained in these examples, NMR means nuclear magnetic resonance spectrum, MS means mass analysis spectrum, and IR means infrared absorption spectrum.

EXAMPLE 1

(Synthesis of Compound No. 1)

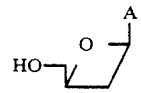

1-1. (Syntheses of Compounds ② and ③)

Into a solution of 123 mg of N(6)-benzoyl-9-(2-deoxy-2-hydroxymethyl-β-D-erythroxetanyl)-adenine (Compound ①) ($P_2$=$COC_6H_5$) in 1 ml of anhydrous dimethylformamide are successively added 70 mg of imidazole and 60 mg of tert-butyldimethylsilyl chloride in the form of a solution in 2 ml of anhydrous dimethylformamide. After stirring the resulting mixture at room temperature for 2 hours, the solvent is distilled off under reduced pressure, the residue is diluted with 20 ml of water, and it is extracted with chloroform. The chloroform extract is washed with saturated aqueous solution of sodium chloride and dried over anhydrous magnesium sulfate.

After filtering off the magnesium sulfate, the solvent is distilled off under reduced pressure to obtain a light yellow syrup. It is passed through a column packed with 20 g of silica gel, and it is eluted with chloroform-methanol (20:1). Then, it is subjected to silica gel thin layer chromatography (TLC) [developing solvent: chloroform-methanol (10:1)], fractions having Rf value of about 0.46 are collected and the solvent is distilled off therefrom under reduced pressure to obtain 49.6 mg (30.6%) of Compound ② ($P_2$= $COC_6H_5$,

Further, fractions having Rf value of about 0.60 are collected and the solvent is distilled off therefrom under reduced pressure to obtain 25.3 mg (16.0%) of Compound ③ ($P_2$=$COC_6H_5$,

Compound ②: MS m/z: 470 M+H)+; NMR (400 MHz, CDCl₃, TMS) ppm: 9.23 (1H, s, NH), 8.78 (1H, s, 8-H), 8.68 (1H, s, 2-H), 8.03 (2H, d, J=7.5 Hz, Ph), 8.50–8.63 (3H, m, Ph), 6.60 (1H, d, J=5.6 Hz, 1'-H), 4.73 (1H, m, 3'-H), 3.93–4.70 (3H, m, OH,

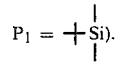

3.81 (1H, dd, J=11.7 Hz, 2.8 Hz), 3.58–3.72 (2H, m, 2'-H,

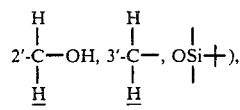

0.92 (9H, s,

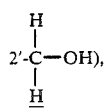

0.10 (3H, s,

0.12 (3H, s,

Compound ③: MS m/z: 470 (M+H)+; NMR (400 MHz, CDCl₃, TMS) ppm: 9.34 (1H, s, NH), 8.79 (1H, s, 8-H), 8.34 (1H, s, 2-H), 8.35 (2H, d, J=7.5 Hz, Ph), 7.48–7.63 (3H, m, Ph), 6.50 (1H, d, J=5.7 Hz, 1'-H), 5.50 (1H, broad s, —OH), 4.04 (2H, m, 3'—CH₂OH), 3.67-3.87 (3H, m, 2'-H, 2'—CH₂OH), 0.91 (9H, s,

0.10 (6H, s,

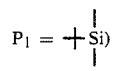

1-2. (Synthesis of compound ④)

Methanesulfonyl chloride (13.2 microliters) is added to a solution of 61.7 mg of Compound ② ($P_2$= $COC_6H_5$, $P_1 = +\overset{|}{\underset{|}{Si}})$ in 3 ml anhydrous pyridine, while cooling the mixture with ice and stirring it, after which the resulting mixture is stirred at room temperature for 2 hours.

The solvent is distilled off under reduced pressure from the reaction mixture, the residue is diluted with 10 ml of water and it is extracted twice with each 10 ml portions of chloroform. The chloroform extract is washed with saturated aqueous solution of sodium chloride and dried over anhydrous sodium sulfate.

After filtering off the sodium sulfate, the solvent is distilled off under reduced pressure to obtain a colorless syrup. It is separated by silica gel column chromatography (20 ml, chloroform-methanol 50:1). Then, it is subjected to silica gel TLC [developing solvent: chloroform-methanol (20:1)]. Fractions having Rf value of about 0.50 are collected, the solvent is distilled off under reduced pressure, and there is obtained 61.3 mg (85.5%) of Compound ④ as a colorless powder.

Compound ④: NMR (60 MHz, CDCl₃, TMS) ppm: 9.31 (1H, s, NH), 8.65 (1H, s, 8-H), 8.53 (1H, s, 2-H), 7.76–8.10 (2H, m, Ph), 7.30–7.61 (3H, m, Ph), 6.53 (1H, d, J=6.0 Hz, 1'-H), 4.38–4.83 (3H, m, 3'-H, 2'—CH₂), 3.53-4.20 (3H, m, 2'-H, 3'—CH₂), 3.03 (3H, s, 0.87 (9H, s, 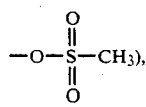

0.13 (6H, s, 

1-3. (Synthesis of Compound ⑤)

A solution of 330 mg of potassium tertbutoxide in 10 ml of anhydrous tetrahydrofuran is added to a solution of 484 mg of Compound ④ ($P_2$=COC$_6$H$_5$,

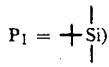

in 10 ml of anhydrous tetrahydrofuran, while cooling the mixture with ice and stirring it. The resulting mixture is stirred at room temperature for 2 hours. Then, 0.4 ml of acetic acid is added to the reaction mixture while cooling it with ice, after which the solvent is distilled off under reduced pressure, the residue is diluted with 50 ml of water, and it is extracted twice with each 50 ml portions of chloroform. The chloroform extract is washed with saturated aqueous solution of sodium chloride and dried over anhydorus sodium sulfate. After filtering off the sodium sulfate, the solvent is distilled off under reduced pressure to obtain a light yellow syrup. It is separated by silica gel column chromatography (60 ml, chloroform-methanol 50:1). Then, it is subjected to silica gel TLC [developing solvent: chloroform-methanol (20:1)]. Fractions having Rf value of about 0.79 are collected and the solvent is distilled off under reduced pressure to obtain 309.4 mg (77.6%) of Compound ⑤ as a colorless powder.

Compound ⑤: MS m/z: 450 (M-H)$^+$; NMR (400 MHz, CDCl$_3$, TMS) ppm: 9.27 (1H, s, NH), 8.12 (1H, s, 8-H), 8.68 (1H, s, 2-H), 8.22 (2H, d, J=8.0 Hz, Ph), 7.48-7.63 (3H, m, Ph), 7.15 (1H, s, 1'-H), 5.25-5.36 (3H, m, 2'—CH$_2$=, 3'-H), 3.96-4.10 (2H, m, 3'—CH$_2$), 0.92 (9H, s,

0.13 (6H, s,

1-4. (Synthesis of Compound ⑥)

Under a stream of nitrogen gas, a solution of 580 mg sodium periodate in acetone (3.5 ml)-water (3.5 ml) and a solution of 84 mg potassium permanganate in 4 ml of water were added to a solution of 400 mg of Compound ⑤ ($P_2$=COC$_6$H$_5$, $P_1 = +\overset{|}{\underset{|}{Si}})$ in 4 ml of acetone while cooling the mixture with ice- and stirring it, and the resulting mixture is stirred at room temperature for 2 hours.

While cooling the mixture with ice, a solution of sodium sulfite is added thereto to decompose the excessive potassium permanganate. Then, 30 ml of acetone is added to the reaction mixture and the precipitate is filtered off. The filtrate is concentrated under reduced pressure, and the acetone is distilled off. The remaining aqueous solution is diluted with 60 ml of water and extracted thrice with each 50 ml portions of chloroform.

The chloroform extract is washed with a saturated aqueous solution of sodium chloride and dried over anhydrous sodium sulfate. After filtering off the sodium sulfate, the solvent is distilled off under reduced pressure to obtain 360 mg of Compound ⑨

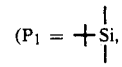

$P_2$=COC$_6$H$_5$) as a light brown colored syrup. Then, 28 mg of sodium boron hydride is added to 20 ml of a methanolic solution containing 360 mg of Compound ⑨ while cooling the mixture with ice, after which it is stirred at room temperature for 30 minutes. After adding 0.05 ml of acetic acid to the reaction mixture, it is concentrated to dryness under reduced pressure. The residue is diluted with 30 ml of water and extracted thrice with each 30 ml portions of chloroform.

The chloroform extract is washed with saturated aqueous solution of sodium chloride and dried over anhydrous sodium sulfate. After filtering off the sodium sulfate, the solvent is distilled off under reduced pressure.

The residue is separated by silica gel column chromatography [50 ml, chloroform-methanol (20:1)]. Then it is subjected to silica gel TLC [developing solvent chloroform-methanol (20:1)]. Fractions having Rf value of about 0.53 are collected and the solvent is distilled off under reduced pressure to obtain 236 mg (65.6%) of Compound ⑥ as a colorless powder.

Compound ⑥: NMR (400 MHz, CDCl$_3$, TMS) ppm: 9.12 (1H, s, NH), 8.76 (1H, s, 8-H), 8.56 (1H, s, 2-H), 8.30 (2H, d, J=8.1 Hz, Ph), 7.48-7.67 (3H, m, Ph), 6.72 (1H, d, J=4.8 Hz, 1'-H), 5.13-5.27 (2H, m, 2'-H, 2'—OH), 4.98 (1H, m, 3'-H), 4.17–4.30 (2H, m, 3'—CH₂), 0.93 (9H, s,

0.17 (6H, s,

1-5. (Synthesis of Compound ⑦)

Under a stream of nitrogen gas, 53 mg of 4-dimethylaminopyridine and 63 microliters of phenyl chlorocarbonothionate are added to a solution of 50 mg of Compound ⑥ (P₂=COC₆H₅,

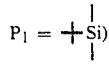

in 3 ml of anhydrous acetonitrile while cooling the mixture with ice and stirring it, after which the mixture is stirred at room temperature for 18 hours. After distilling off the solvent under reduced pressure, the residue is diluted with 10 ml of water and it is extracted thrice with each 10 ml portions of chloroform. The chloroform extract is washed with saturated aqueous solution of sodium chloride and dried over anhydrous sodium sulfate. After filtering off the sodium sulfate, the solvent is distilled off under reduced pressure to obtain a syrup. The syrup is purified by silica gel column chromatography (20 ml, chloroform-methanol 50:1). Then, the purified product is subjected to silica gel thin layer chromatography (TLC) (developing solvent: chloroform-methanol 20:1), fractions having Rf value of about 0.567 are collected, and the solvent is distilled off therefrom under reduced pressure to obtain 53.8 mg (82.7%) of Compound ⑦ as a colorless powder.

Compound ⑦: NMR (60 MHz, CDCl₃, TMS) ppm: 9.04 (1H, s, NH), 8.67 (1H, s, 8-H), 8.56 (1H, s, 2-H), 7.85–8.17 (2H, M, Ph), 6.67–7.67 (9H, m, Ph,

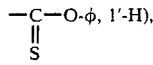

1'-H), 6.17 (1H, m, 2'-H), 5.14 (1H, m, 3'-H), 4.17 (2H, m, 3'—CH₂), 0.93 (9H, s,

0.17 (6H, s,

1-6. (Synthesis of Compound No. 1) (including the synthesis of Compound ⑧)

Under a stream of nitrogen gas, 135 microliters of tributyltin hydride and a catalytic quantity of α,α'-azobisisobutyronitrile are added to a solution of 90 mg of Compound ⑦ (P₂=COC₆H₅,

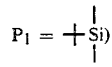

in 3 ml of anhydrous acetonitrile, and the resulting mixture is stirred at 90° C. for 2 hours. The solvent is distilled off under reduced pressure to obtain a syrup. The syrup is purified by silica gel column chromatography (50 ml, chloroform-methanol 50:1). Then, the purified product is subjected to silica gel TLC (developing solvent: chloroform-nethanol 20:1), fractions having Rf value of about 0.52 are collected and the solvent is distilled off under reduced pressure to obtain 58 mg of crude Compound ⑧ as a colorless syrup.

Elimination of protecting group: A solution of tetrabutylammonium fluoride in tetrahydrofuran (0.3 ml, 1.05M) is added to a solution of 58 mg of crude Compound ⑧ in 3.5 ml of tetrahydrofran, and the resulting mixture is stirred at room temperature for one hour. The solvent is distilled off from the reaction mixture under reduced pressure, and the residue is stirred at 60° C. for one hour together with 2 ml of methanol and 4 ml of concentrated ammonia water. After distilling off the solvent from the reaction mixture under reduced pressure, the residue is dissolved into 3 ml of methanol, mixed with 200 mg of silica gel and methanol is distilled off under reduced pressure. The residue is subjected to a silica gel column chromatography (25 ml) previously equilibrated with chloroform-methanol (8:1) and eluted with chloroform-methanol (8:1, 4:1). The eluted product is subjected to silica gel TLC (developing solvent: chloroform-methanol, 4:1), fractions having Rf value of about 0.44 are collected and the solvent is distilled off therefrom under reduced pressure. The residue is dissolved into aqueous methanol (80%) and purified by column chromatography using 100 ml of Sephadex® LH-20 equilibrated with the same solvent as above. The purified product is subjected to the same silica gel TLC as above, fractions having Rf value of about 0.44 are collected and the solvent is distilled off therefrom under reduced pressure to obtain 5.6 mg (17.2%) of Compound No. 1 as a colorless powder.

Compound No. 1: MS m/z: 221 (M⁺); NMR (400 MHz, D₂O) ppm: 8.84 (1H, s, 8-H), 8.07 (1H, s, 2-H), 6.58 (1H, dd, J=7.0 Hz, J=7.0 Hz, 1'-H), 4.93 (1H, m, 3'-H), 3.68–3.86 (2H, m, 3'—CH₂OH), 3.12–3.33 (2H, m, 2'—CH₂)

EXAMPLE 2

(Synthesis of Compound No. 2)

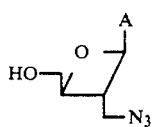

Under a stream of nitrogen gas, 17 mg of sodium nitride is added to a solution of 56 mg of Compound ④ ($P_2=COC_6H_5$,

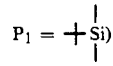

in 1 ml of anhydrous dimethylformamide, and the resulting mixture is stirred at 100° C. for 20 minutes. After distilling off the solvent from the reaction mixture under reduced pressure, the residue is separated by silica gel column chromatography (20 ml, chloroform-methanol 50:1). In silica gel TLC (developing solvent chloroform-methanol 20:1), fractions having Rf value of about 0.68 are collected and the solvent is distilled off therefrom under reduced pressure. The residue is treated (elimination of protecting group) in the same as in 1-6 of Example 1 ($P_2=COC_6H_5$,

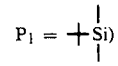

to obtain 19.8 mg (69.7%) of Compound No. 2 as a colorless powder.

Compound No. 2 : MS m/z: 276 (M+); IR$\nu_{max}^{KBr}$ cm$^{-1}$: 3100-3600, 2100, 1690, 1620; NMR (60 MHz, CD$_3$OD, TMS) ppm: 8.57 (1H, s, 8-H), 8.15 (1H, s, 2-H), 6.40 (1H, d, J=5.82 Hz, 1'-H), 4.60 (1H, m, 3'-H), 3.50-3.92 (5H, m)

EXAMPLE 3

(Synthesis of Compound No. 3)

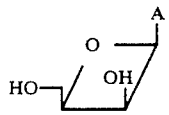

Protecting groups are eliminated from 24 mg of Compound ⑥ ($P_2=COC_6H_5$,

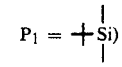

in the same manner as in 1-6 of Example 1 to obtain 9.4 mg (80.0%) of Compound No. 3 as a colorless powder.

Compound No. 3: MS m/z: 238 (M+H)+; NMR (400 MHz, D$_2$O) ppm: 8.53 (1H, s, 8-H), 8.15 (1H, s, 2-H), 6.78 (1H, d, J=5.2 Hz, 1'-H), 5.21 (1H, m, 2'-H), 5.07 (1H, m, 3'-H), 3.93-4.08 (2H, m, 3'—CH$_2$OH)

EXAMPLE 4

(Synthesis of Compound No. 4)

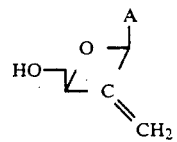

Protecting groups are eliminated from 38 mg of Compound ⑤ ($P_2=COC_6H_5$,

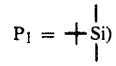

in the same manner as in 1-6 of Example 1 to obtain 18.5 mg (94%) of Compound No. 4 as a colorless powder.

Compound No. 4 : MS m/z: 233 (M+); NMR (60 MHz, CD$_3$OD, TMS) ppm: 8.73 (1H, s, 8-H), 8.33 (1H, s, 2-H), 7.20 (1H, s, 1'-H), 5.50 (2H, broad, 2'—CH$_2$=), 3.90-4.30 (3H, m, 3'-H, 3'—CH$_2$OH)

EXAMPLE 5

(Synthesis of Compound No. 5)

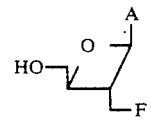

Under a stream of nitrogen gas, 160 microliters of diethylaminosulfur trifluoride is added to a solution of 101 mg of Compound ② ($P_2=COC_6H_5$,

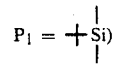

in 4 ml of anhydrous dichloromethane while cooling the mixture to −30° C. and stirring it for 4 hours. Then, 10 ml of chloroform and 0.2 ml of concentrated ammonia water are added to the reaction mixture and the solvent is distilled off under reduced pressure, after which the residue is diluted with 10 ml of water and extracted thrice with each 10 ml portions of chloroform. The chloroform extract is washed with saturated aqueous solution of sodium chloride and dried over anhydrous sodium sulfate. After filtering off the sodium sulfate, the solvent is distilled off under reduced pressure to obtain a syrup. The syrup is purified by silica gel column chromatography (25 ml, chloroform-methanol, 40:1). Then, the purified product is subjected to silica gel TLC (developing solvent: chloroform-methanol 10:1), fractions having Rf value of about 0.71 are collected and the solvents are distilled off therefrom to obtain 71 mg of a residue (protected compound of Compound No. 5). Its protecting groups are eliminated in the same manner as in 1-6 of Example 1 to obtain 9.4 mg (17.3%) of Compound No. 5 as a colorless powder.

Compound No. 5: MS m/z: 253 (M+); NMR (400 MHz, D$_2$O) ppm: 8.54 (1H, s, 8-H), 8.17 (1H, s, 2-H), 6.58 (1H, d, J=6.30 Hz, 1'-H), 4.98 (1H, m, 3'-H), 4.63–4.80 (2H, m, 2′—CH₂OH), 3.79–4.06 (3H, m, 2′-H, 2′—CH₂OH)

EXAMPLE 6

(Synthesis of Compound No. 6)

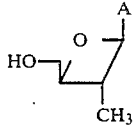

Under a stream of nitrogen gas, 67 microliters of phenyl chlorothionocarbonate is added to a solution containing 114 mg of Compound ② (P₂=COC₆H₅,

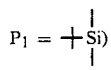

and 88 mg of dimethylaminopyridine in 2 ml of anhydrous acetonitrile, and the resulting mixture is stirred at room temperature for 3 hours. After adding 0.5 ml of methanol to the reaction mixture, the solvent is distilled off under reduced pressure, and the residue is diluted with 10 ml of water and extracted thrice with each 10 ml portions of chloroform.

The chloroform extract is washed with saturated aqueous solution of sodium chloride and dried over anhydrous sodium sulfate. After filtering off the sodium sulfate, the solvent is distilled off under reduced pressure to obtain a syrup. The syrup is purified by silica gel column chromatography (20 ml, chloroform-methanol 40:1). The purified product is subjected to silica gel TLC (developing solvent: chloroform-methanol 20:1), fractions having Rf value of about 0.73 are collected and the solvent is distilled off therefrom under reduced pressure to obtain 78.7 mg of a residue. Under a stream of nitrogen gas, 110 microliters of tributyltin hydride and a catalytic quantity of α, α′-azobisisobutyronitrile are added to a solution of 78.7 mg of the residue in 3 ml of anhydrous toluene, and the resulting mixture is stirred at 85° C. for 45 minutes. The solvent is distilled off under reduced pressure, and the residue is purified by silica gel column chromatography (40 ml, developing solvent: chloroform-methanol 40:1). Then, the purified product is subjected to silica gel TLC (developing solvent chloroform-methanol 20:1), fractions having Rf value of about 0.59 are collected and the solvent is distilled off therefrom under reduced pressure to obtain 47 mg of a syrup (protected compound of Compound No. 6). Its protecting groups are eliminated in the same manner as in 1-6 of Example 1 to obtain 9.3 mg (16.7%) of Compound No. 6 as a colorless powder.

Compound No. 6: MS m/z: 235 (M⁺); NMR (400 MHz, D₂O) ppm: 8.58 (1H, s, 8-H), 8.13 (1H, s, 2-H), 6.24 (1H, d, J=6.36 Hz, 1′-H), 4.53 (1H, m, 3′-H), 3.74–3.86 (2H, m, 3′—CH₂OH), 3.60 (1H, m, 2′—H), 1.30 (3H, d, —CH₃)

EXAMPLE 7

(Synthesis of Compound No. 7)

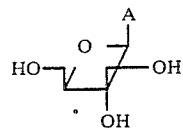

To a solution of 42 mg of Compound ⑤ (P₂=COC₆H₅,

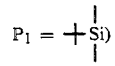

in tetrahydrofuran (2 ml)-water (1 ml) are added 0.2 ml of 1% aqueous solution of osmium tetraoxide and 60 mg of sodium periodate, and the resulting mixture is stirred at room temperature for 17 hours. The reaction mixture is diluted with 10 ml of water and extracted thrice with each 10 ml portions of chloroform.

The chloroform extract is washed with saturated aqueous solution of sodium chloride and dried over anhydorus sodium sulfate. After filtering off the sodium sulfate, the solvent is distilled off under reduced pressure to obtain a syrup. The syrup is purified by silica gel column chromatography (20 ml, chloroform-methanol 20:1). Then, the purified product is subjected to silica gel TLC (developing solvent: chloroform-methanol 20:1), fractions having Rf value of about 0.13 are collected, from which the solvent is distilled off under reduced pressure to obtain 35 mg of a residue (protected compound of Compound No. 7). Protecting groups are eliminated from the protected compound in the same manner as in 1-6 of Example 1 to obtain 17.8 mg (72.4%) of Compound No. 7 as a colorless powder.

Compound No. 7: MS m/z: 268 (M+H)⁺; NMR (400 MHz, D₂O, 50° C.) ppm: 8.74 (1H, s, 8-H), 8.52 (1H, s, 2-H), 6.83 (1H, s, 1′—H), 5.14 (1H, t, J=4.8 Hz, 3′—H), 4.32 (2H, d, J=4.98 Hz, 3′—CH₂OH), 3.99-4.13 (2H, d×2, J=12.0 Hz, 2′—CH₂OH)

EXAMPLE 8

(Synthesis of Compound No. 8)

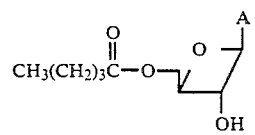

Fourty five microliters of valeryl chloride is added to a solution of 37.7 mg of Compound ③ (P₂=H,

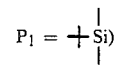

in 2 ml of anhydrous pyridine, and the resulting mixture is stirred at room temperature for 18 hours. The solvent is distilled off from the reaction mixture under reduced pressure The residue is purified by silica gel column chromatography (20 ml, chloroform-methanol 50:1) to obtain a compound of Formula ③ (P₂=H,

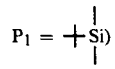

of which 3'-hydroxyl group has been valerylated, as a syrup. P₁ is eliminated from the compound in the same manner as in 1-6 of Example 1 to obtain 21.4 mg (65.8%) of Compound No. 8 as a colorless powder.

Compound No. 8: MS m/z: 335 (M+); NMR (60 MHz, CD₃OD, TMS) ppm: 8.43 (1H, s, 8-H), 8.20 (1H, s, 2-H), 6.50 (1H, d, J=5.2 Hz, 1'-H), 4.48 (2H, m, 3'—CH₂OH), 3.62-4.00 (3H, m, 3'-H, 2'—CH₂OH), 0.70-2.70 (9H,

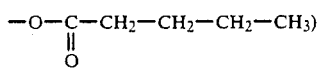

EXAMPLE 9

(Synthesis of Compound No. 9)

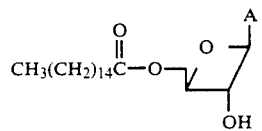

Thirty microliters of palmityl chloride is added to a solution of 16.2 mg of Compound ③ (P₂=H,

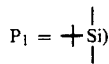

in 2 ml of anhydrous pyridine, and the resulting mixture is stirred at room temperature. The product is treated in the same manner as in Example 8 to obtain 14 mg (69.6%) of Compound No. 9.

Compound No. 9: MS m/z: 490 (M+H)+; NMR (60 MHz, CD₃OD+CDCl₃, TMS) ppm: 8.60 (1H, s, 8-H), 7.98 (1H, s, 2-H), 6.66 (1H, d, J=5.4 Hz, 1'—H), 4.60-4.72 (2H, m, 3'—CH₂OH), 3.95-4.15 (3H, m, 3'—H, 3'—CH₂OH), 1.05-2.60 [31H,

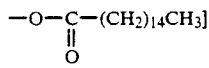

EXAMPLE 10

(Synthesis of Compound No. 10)

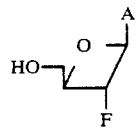

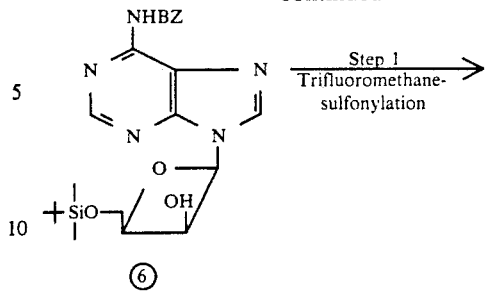

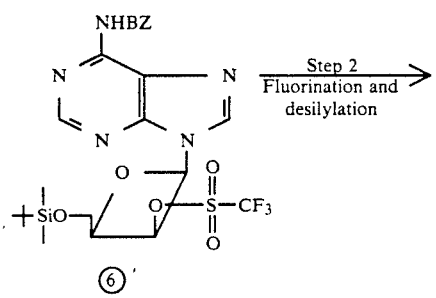

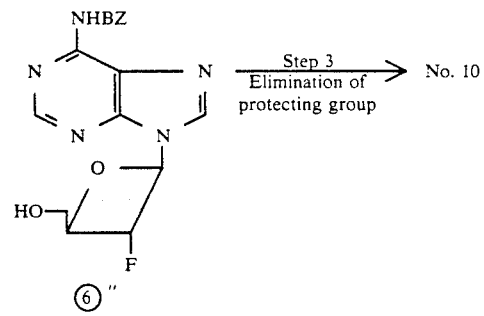

(1) Synthesis of Compound ⑥'

To a solution of 36.6 mg of Compound ⑥ in 1 ml of anhydrous dichloromethane are added 9.8 mg of cimethylaminopyridine, 22.2 microliters of triethylamine and 17 microliters of trifluoromethanesulfonyl chloride, and the resulting mixture is stirred at room temperature for one hour. The solvent is distilled off under reduced pressure to obtain a residue.

The residue is passed through a 7 g silica gel column and eluted with chloroform-methanol (25:1). In silica gel TLC (developing solvent: chloroform-methanol 10:1), fractions having Rf value of about 0.66 are collected, from which the solvent is distilled off under reduced pressure to obtain 34 mg (72.4%) of Compound ⑥'.

(2) Synthesis of Compound ⑥"

Under a stream of nitrogen, a solution of 80 mg of tris(dimethylamino)sulfur difluorotrimethyl silicate in 0.5 ml of anhydrous dichloromethane is added to a solution of 34 mg of Compound ⑥' in 1 ml of anhydrous dichloromethane and stirred for 2.5 hours while cooling the mixture to −78° C. Then, 3 ml of water is added to the reaction mixture and it is extracted thrice with each 5 ml portions of chloroform. The organic layer is washed with saturated aqueous solution of sodium chloride and dried over anhydrous sodium sulfate. After filtering off the sodium sulfate, the solvent is distilled off under reduced pressure to obtain a syrup. The syrup is subjected to silica gel thin layer chromatography (MERCK, art. 5744, two sheets, chloroformmethanol, 10:1). Fractions having Rf value of about 0.35 are collected and eluted with chloroform-methanol (5:1) by the use of glass filter. The eluate is concentrated to dryness under reduced pressure to obtain 2.8 mg of Compound ⑥".

Compound ⑥": NMR (400 MHz, CDCl₃, TMS) ppm: 9.09 (1H, br, s, NH), 8.83 (1H, s, 8-H), 8.22 (1H, s, 2-H), 8.04 (2H, d, J=8.2 Hz, ph), 7.52-7.767 (3H, m, ph), 6.50 (1H, dd, J=4.8 Hz, 12.8 Hz, 1'-H), 6.17-6.36 (1H, m, 2'-H), 4.90 (1H, m, 3'-H), 3.96-4.28 (2H, m)

(3) Synthesis of Compound No. 10

Compound ⑥" (2.8 mg) is dissolved into a mixture consisting of 1.5 ml of methanol and 1.5 ml of concentrated ammonia water and stirred at 50° C. for 2.5 hours. The reaction mixture is concentrated to dryness under reduced pressure, and the residue is dissolved into aqueous methanol (80%) and purified by column chromatography using Sephadex ® LH-20 (100 ml) previously equilibrated with the same solvent as above. The purified product is subjected to silica gel TLC (chloroform-methanol, 5:1), fractions having Rf value of about 0.5 are collected, the solvent is distilled off therefrom under reduced pressure, and the residue is purified by silica gel column chromatography (20n ml, chloroform-methanol, 10:1) to obtain 1.0 mg of Compound No. 10.

Compound No. 10: NMR (400 MHz, D₂O) ppm: 8.39 (1H, s, 8-H), 8.19 (1H, s, 2-H), 6.64 (1H, dd, J=4.4 Hz, 13.5 Hz, 1'-H), 5.88-6.07 (1H, m, 2'-H), 4.88-4.97 (1H, m, 3'-H), 3.92-3.96 (2H, m, 3'—CH₂OH)

EXAMPLE 11

(Synthesis of Compound No. 11)

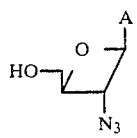

Under a stream of nitrogen, 10 mg of sodium azide is added to a solution of 32 mg of Compound ⑥' in 1 ml anhydrous DMF, and the resulting mixture is stirred at 80° C. for 3 hours. The solvent is distilled off from the reaction mixture under reduced pressure to obtain a residue (protected compound of Compound No. 11). Protecting groups are eliminated from the protected compound in the same manner as in 1-6 of Example 1 to obtain 10.7 mg (yield 75.7%) of Compound No. 11 as a colorless powder.

Compound No. 11 : NMR (400 MHz, CD₃OD, TMS) ppm: 8.53 (1H, s, 8-H), 8.23 (1H, s, 2-H), 6.40 (1H, d, J=5.1 Hz, 1'-H), 5.34 (1H, m, 2'-H), 4.63 (1H, m, 3'-H), 3.82-3.98 (2H, m)

EXAMPLE 12

Synthesis of Compound No. 12)

Synthesis of

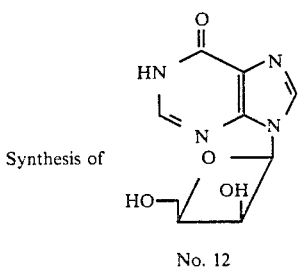

No. 12

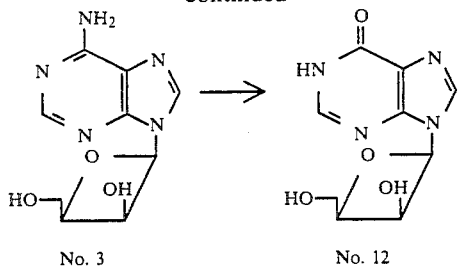

No. 3     No. 12

(I) Adenosine deaminase (29 microliters, 42.3 units) (manufactured by Sigma Co., EC 3.5.4.4) is added to a solution of 20.4 mg of Compound No. 3 in 10.2 ml of 1/10M phosphate buffer, and the mixture is stirred at 27° C. for 5 days. The reaction mixture is passed through a column packed with 30 ml of MCI ® GEL CHP20P to have the product adsorbed on the column. After washing the column with water, the adsorbed matter is eluted with 90 ml of methanol containing 20% water. The eluted product is subjected to silica gel TLC (Art. 5715, manufactured by MERCK) [developing solvent 1-butanol-acetic acid-water (4:1:2)], and fractions having Rf value of about 0.40 are collected, from which the solvent is distilled off under reduced pressure to obtain 19.1 mg (yield 93.2%) of Compound No. 12 as a colorless powder.

Compound No. 12 : MS m/z: 239 (M+H)⁺; NMR (400 MHz, D₂O) ppm: 8.51 (1H, s, 8-H), 8.13 (1H, s, 2-H), 6.80 (1H, d, J=4.8 Hz, 1'-H), 5.23-5.20 (1H, m, 2'-H), 5.10-5.06 (1H, m, 3'-H), 4.07-3.95 (2H, m, 3'—CH₂OH)

(II) It is also possible to obtain Compound No. 12 by using alive cell having adenosine deaminase or its treated product in place of said adenosine deaminase, as mentioned below.

Thus, 100 ml of a medium (pH 7.0) containing 0.3% of meat extract, 1.0% of peptone and 0.7% of sodium chloride is dividingly poured into 500 ml Erlenmeyer flasks and sterilized in autoclave at 120° C. for 20 minutes. One platinum loop quantity of *Escherichia coli* NIHJ is inoculated into each of the flasks and subjected to aerobic shaking culture at 37° C. for 18 hours. Then, 1,000 ml of the culture fluid is centrifuged at 10,000 r.p.m. for 10 minutes to collect the alive cell. After twice or thrice washing the cell with an equal volume of 1/20M phosphate buffer (pH 7.0), it is suspended into 100 ml of the same buffer as above. Then, 50 mg of Compound No. 3 is added to the suspension and reacted with shaking at 37° C. for 18 hours, after which the reaction mixture is heated at 100° C. for 5 minutes to stop the reaction. The reaction mixture is centrifuged under the same conditions as above, and the resulting supernatant is passed through a column packed with 50 ml of MCI ® GEL CHP20P to have the product adsorbed on the column. The column is washed with water, the adsorbed matter is eluted with 150 ml of methanol containing 20% water, and the solvent is distilled off therefrom under reduced pressure to obtain 46 mg (yield 91.6%) of Compound No. 12 as a colorless powder.

The Adenosine deaminase used in this Example may be a commercial product, of which one concrete example is EC 3.5.4.4 manufactured by Sigma Co. Apart from it, products collected from animal tissues, cultured microorganisms, adenosine deaminase collected from them, and the like may all be usable regardless of their origin, so far as they are known to have a similar ability. A purified enzyme is not needed for this invention. When an enzyme originated from microorganism is to be used, a cultured product of microorganis (cell) obtained by culturing an organism having an ability to produce Adenosine deaminase in a nutrient medium can be used as it is. Apart from them, crude enzyme samples prepared from acetone-dried product of microorganism, ground product of microorganism cell, its ultrasonic wave-treated product, its product treated with surfactant, toluene or lysozyme and the like, as well as cells immobilized on natural and synthetic polymers, are also usable similarly. Concretely speaking, the following microorganisms can be used.

Alkaligenes bookeri IFO 12948
Escherichia coli NIJH
Escherichia coli 120551
Escherichia coli 120595
Escherichia coli 120628
Citrobacter freundii GN346
Proteus morganii IFO 3168
Elytrosporanim brasiliense IFO 1259
Nocardia asteriodes IFO 3423
Streptomyces alboniger IFO 12738
Streptomyces californicus IFO 12750
Streptomyces chrestomyceticus IFO 13444
Streptomyces subsp lasaliensis ATCC 31180
Streptomyces tubercidicus IFO 13090
Streptomyces verticillus ATCC 31307
Aspergillus niger IFO 4066
Fusarium roseum IFO 7189
Penicillium chrysogenum JBI-FI
Penicillium chrysogenum 51-20T

EXAMPLE 13

(Synthesis of Compound No. 13)

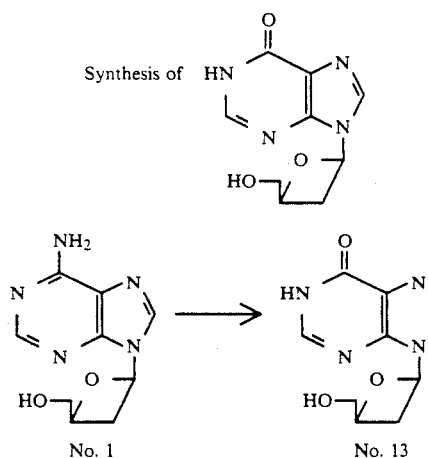

Compound No. 1 (3.5 mg) is dissolved into 1.75 ml of 1/10M phosphate buffer, to which is added 10 microliters (14.6 units) of Adenosine deaminase (EC 3.5.4.4, manufactured by Sigma Co.). The resulting mixture is stirred at 37° C. for 4.5 hours.

The reaction mixture is passed through a column packed with 6.5 ml of MCI ® GEL 'CHP$_{20}$P to have the product adsorbed thereon. After washing the column with water, the adsorbed matter is eluted with 20 ml of methanol containing 20% of water. The eluted product is subjected to silica gel TLC (Art. 5715, manufactured by MERCK) [developing solvent: 1-butanol-acetic acid-water (4:1:2)], fractions having Rf value of about 0.36 are collected and the solvent is distilled off therefrom to obtain 3.34 mg (yield 95.0%) of Compound No. 13 as a colorless powder.

Compound No. 13: MS m/z: 222 (M+); NMR (400 MHz, D$_2$O) ppm: 8.49 (1H, s, 8-H), 8.12 (1H, s, 2-H), 6.64 (1H), dd, J=7.0 Hz, J=7.0 Hz, 1'-H), 4.94 (1H, m, 3'-H), 3.86–3.73 (2H, m, 3'—C$\underline{H}_2$OH), 3.32–3.15 (2H, m, 2'—CH$_2$—)

EXAMPLE 14

(Synthesis of Compound No. 14)

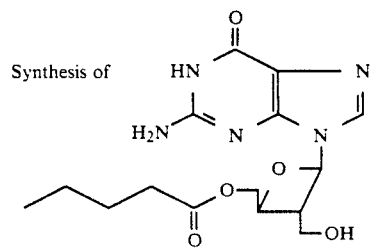

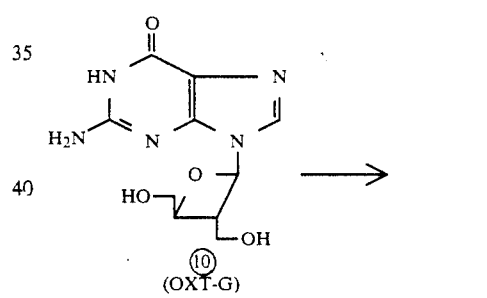

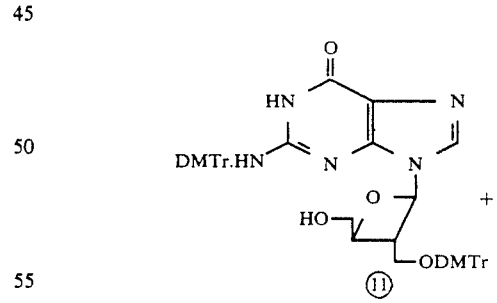

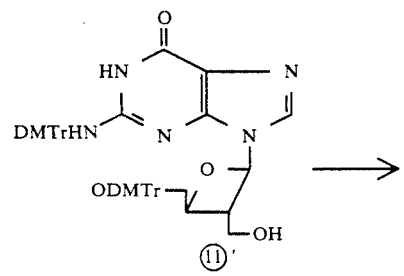

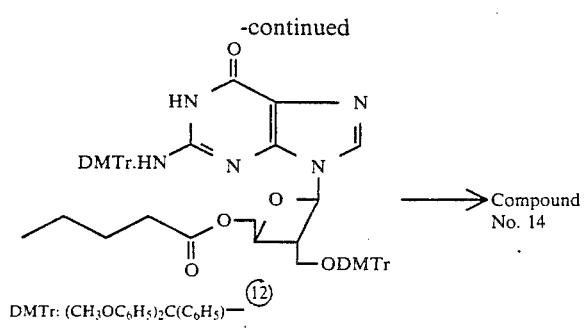

→ Compound No. 14

DMTr: (CH₃OC₆H₅)₂C(C₆H₅)—

Under a stream of nitrogen gas, 0.52 mg of 4-dimethylaminopyridine, 86.7 microliters of triethylamine and 139.3 mg of 4,4'-dimethoxytrityl chloride are added to a solution of 50 mg of Compound ⑩ (oxetanocin G: OXT-G) in 1.6 ml of anhydrous dimethylformamide. The resulting mixture is stirred in the dark at room temperature for 24 hours. After distilling off the solvent under reduced pressure, the syrup obtained as a residue is purified by silica gel column chromatography (20 ml, chloroform-methanol 50:1). The purified product is subjected to silica gel TLC (developing solvent: chloroform-methanol 10:1), fractions having Rf value of about 0.51 are collected and the solvent is distilled off therefrom under reduced pressure to obtain 27.1 mg (yield 16.6%) of Compound ⑪ as a colorless powder Further, fractions having Rf value of about 0.64 are collected and the solvent is distilled off under reduced pressure to obtain 42.0 mg (yield 25.8%) of Compound ⑪'.

Under a stream of nitrogen gas, 0.4 mg of 4-dimethylaminopyridine, 19.2 microliters of triethylamine and 10.9 microliters of valeryl chloride are added to a solution of 30 mg of Compound ⑪ in 1 ml of anhydrous dichloromethane, and the resulting mixture is stirred at room temperature for 1.5 hours. After distilling off the solvent under reduced pressure, the syrup obtained as a residue is purified by silica gel column chromatography (20 ml, chloroform-methanol, 60:1). The purified product is subjected to silica gel TLC (developing solvent: chloroform-methanol, 20:1), fractions having Rf value of about 0.38 are collected and the solvent is distilled off therefrom under reduced pressure to obtain 16.2 mg (yield 47.2%) of compound ⑫ as a syrup.

Compound ⑫ : NMR (400 MHz, CDCl₃, TMS) ppm: 7.79 (1H, s), 7.41 (1H, s), 7.39 (1H, s), 7.16–7.30 (18H, m), 6.78–6.83 (8H, m), 6.04 (1H, d, J=5.5 Hz, 1'-H), 4.65 (1H, m, 3'-H), 4.36 (1H, m, 3'—CH₂O-a), 4.18 (1H, m, 3'-(CH₂O-b), 3.77–3.73 (12H, 4×MeO), 3.43 (1H, m, 2'-H), 3.29 (2H, m, 2'—CH₂O—), 2.34 (2H, m), 1.59 (2H, m), 1.29 (2H, m), 0.88 (3H, m)

Compound ⑫ (16.2 mg) is dissolved into 90% aqueous acetic acid and stirred at room temperature for 2.5 hours. After distilling off the solvent under reduced pressure, the syrup obtained as a residue is dissolved into aqueous methanol (80%) and purified by column chromatography using 100 ml of Sephadex ® LH-20 previously equilibrated with the same solvent as above. The purified product is subjected to silica gel TLC (developing solvent: n-butanol-water-acetic acid (4:2:1)), fractions having Rf value of about 0.58 are collected and the solvent is distilled off therefrom under reduced pressure to obtain 5.5 mg (86.4%) of compound No. 14 as a colorless powder.

4.79 (1H, m, 3'-H), 4.46 (2H, m, 3'—CH₂O—), 3.81 (2H, m, 2'—CH₂OH), 3.72 (1H, m, 2'-H), 2.40 (2H, m), 1.59 (2H, m), 1.35 (2H, m), 0.91 (3H, m)

EXAMPLE 15

(Synthesis of Compound No. 15)

Synthesis of 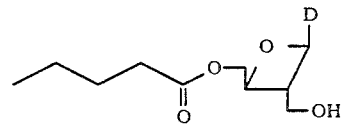

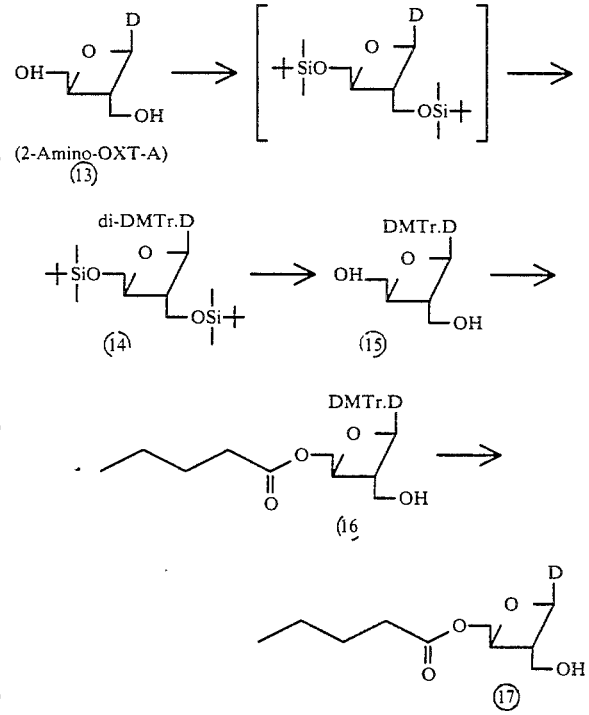

Note:
DMTr: (MeOC₆H₅)₂C(C₆H₅)—
DMTr.D: 2,6-Diaminopurine residue of which either one amino group is protected with DMTr
di-DMTr.D: 2,6-diaminopurine residue of which both amino groups are protected with DMTr Under a stream of nitrogen gas, a solution of 130 mg of imidazole and 150 mg of tert-butyl-dimethylsilyl chloride in 1 ml of anhydrous dimethylformamide is added to a solution of 100 mg of Compound ⑬ (2-Amino-OXT-A) in 2.5 ml of anhydrous dimethylformamide, and the resulting mixture is stirred at room temperature for 2 hours. After distilling off the solvent under reduced pressure, the residue is diluted with 10 ml of water and extracted with chloroform. The chloroform extract layer is washed with saturated aqueous solution of sodium chloride and dried over anhydrous sodium sulfate. After filtering off the sodium sulfate, the solvent is distilled off therefrom under reduced pressure and the syrupy residue thus obtained is purified by silica gel column chromatography [40 ml, 1) chloroform, 2) chloroform-methanol 10:1]. The purified product is subjected to silica gel TLC (developing solvent: chloroform-methanol, 5:1), fractions having Rf value of about 0.90 are collected and dried under reduced pressure to obtain a syrup. Then, the syrup is dissolved into 6 ml of anhydrous dimethylformamide under a stream of nitrogen, 2.3 mg of 4-dimethylaminopyridine, 209.8 microliters of triethylamine and 382.2 mg of 4,4'-dimethoxytrityl chloride are added, and the resulting mixture is stirred in the dark at room temperature overnight. After distilling off the solvent under reduced pressure, the syrupy residue is purified by silica gel column chromatography (20 ml, chloroform-methanol, 100:1). The purified product is subjected to silica gel TLC (developing solvent: chloroform-methahol, 50:1), fractions having Rf value of about 0.73 are collected, and the solvent is distilled off under reduced pressure to obtain 230 mg (yield 55.7%) of compound ⑭.

Compound ⑭ : NMR (200 MHZ, CDCl$_3$, TMS) ppm: 8.03 (1H, S, 8-H), 7.08–7.30, 6.62–6.80 (28H, M, 2×DMT, NH$_2$, NH), 6.22 (1H, d, J=6.2 Hz, 1'-H), 4.54 (1H, m, 3'-H), 3.66–4.00 (4H, m, 2'—CH$_2$, 3'—CH$_2$), 3.71–3.73 (12H, 4×MeO), 0.83–0.88 (18H, 2×t-Bu), 0.00–0.08 (12H, 4×SiMe)

Into 10 ml of tetrahydrofuran is dissolved 230 mg of Compound ⑭ to which is added 241 microliters of 1.0M solution of tetrabutylammonium fluoride in tetrahydrofuran. The resulting mixture is stirred at room temperature for 20 minutes. After distilling off the solvent under reduced pressure, the syrupy residue is purified by silica gel column chromatography (20 ml, chloroform-methanol, 20:1). The purified product is subjected to silica gel TLC (developing solvent: chloroform-methanol, 50:1), fractions having Rf value of about 0.07 are collected, from which the solvent is distilled off under reduced pressure to obtain 137.2 mg (yield 75.3%) of Compound ⑮ as a red-colored power.

Compound ⑮ : NMR (200 MHz, CDCl$_3$, TMS) ppm: 7.57 (1H, S, 8-H), 7.16–7.40, 6.71–7.00 (16H, m, DMTr, NH$_2$, NH), 6.18 (1H, d, J=6.3 Hz, 1'-H), 5.67 (1H, m, 3'-H), 5.36 (2H, br.S, OH), 3.56–4.24 (4H, m, 2'—CH$_2$OH, 3'—CH$_2$OH), 3.75 (6H, s, 2×MeO)

Under a stream of nitrogen gas, 0.3 mg of 4-dimethylaminopyridine, 19.2 microliters of triethylamine and 17.6 microliters of valeryl chloride are added to a solution of 80 mg of Compound ⑮ in 2 ml of anhydrous acetonitrile, and the resulting mixture is stirred at room temperature for 1.5 hours. After distilling off the solvent under reduced pressure, the syrupy residue is purified by silica gel column chromatography (20 ml, chloroform-methanol, 50:1). Then, the purified product is subjected to silica gel TLC (developing solvent: chloroform-methanol 30:1), fractions having Rf value of about 0.34 are collected, and the solvent is distilled off therefrom under reduced pressure to obtain 9.8 mg (yield 10.7%) of Compound ⑯ as a syrup.

Compound ⑯ : NMR (200 MHz, CDCl$_3$, TMS) ppm: 7.83 (1H, S, 8-H), 7.18–7.36, 6.74–6.83 (16H, m, DMTr, NH$_2$, NH), 6.25 (1H, d, J=5.7 Hz, 1'-H), 4.77 (1H, m, 3'-H), 4.36 (2H, m, 3'—CH$_2$), 3.86 (2H, m, 2'—CH$_2$OH), 3.77 (6H, S, 2×Mec), 3.45 (1H, m, 2'-H), 2.34 (2H, m), 1.58 (2H, m), 1.32 (2H, m), 0.89 (3H, m)

Compound ⑯ (9.8 mg) is dissolved into 90% aqueous acetic acid and stirred at room temperature for 30 minutes. After distilling off the solvent under reduced pressure, the syrupy reside is purified by silica gel column chromatography (20 ml, chloroform-methanol, 5:1). Then, the purified product is subjected to silica gel TLC (developing solvent: chloroform-methanol, 5:1), fractions having Rf value of about 0.33 are collected, and the solvent is distilled off therefrom under reduced pressure to obtain 5.0 mg (yield 95.2%) of Compound ⑰ as a syrup.

Compound ⑰ : NMR (200 MHz, CD$_3$OD, TMS) ppm: 8.12 (1H, S, 8-H), 6.32 (1H, 1'-H), 4.78 (1H, m, 3'-H), 4.47 (2H, m, 3'—CH$_2$), 3.70–3.86 (3H, m, 2'-H, 2'—CH$_2$OH), 2.40 (2H, m), 1.58 (2H, m), 1.32( 2H, m), 0.89 (3H, m).

EXAMPLE 16

(Synthesis of Compound No. 16)

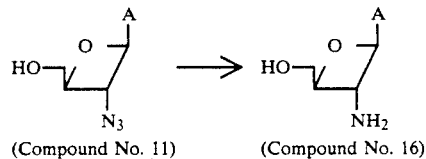

(Compound No. 11)    (Compound No. 16)

Under a stream of nitrogen gas, 10.7 mg of Compound No. 11 is dissolved into a mixture consisting of 3 ml of ethanol, 1 ml of water and 0.4 ml of acetic acid. After adding a catalytic quantity of 10% palladium-carbon thereto, the mixture is stirred at room temperature for 30 minutes. The palladium-carbon is filtered off and the solvent is distilled off, after which the solid product obtained is dissolved into aqueous methanol (80%) and purified by column chromatography using 100 ml of Sephadex® LH-20 previously equilibrated with the same solvent as above. Then, the purified product is subjected to silica gel TLC [developing solvent: n-butanol-water-acetic acid (4:2:1)], fractions having Rf value of about 0.14 and developing a color with ninhydrin are collected, and the solvent is distilled off therefrom under reduced pressure to obtain 3.0 mg (yield 31.3%) of Compound No. 16 as a colorless power.

Compound No. 16 : MS m/z: 237 (MH+); NMR (200 MHz, D$_2$O) ppm: 8.39 (1H, s), 8.12 (1H, s), 6.27 (1H, d, J=5.7 Hz, 1'-H), 4.40–4.90 (2H, m, 3'-H, 2'-H), 3.85 (1H, m, 3'—CH$_2$OH)

EXAMPLE 17

(Synthesis of Compound No. 17)

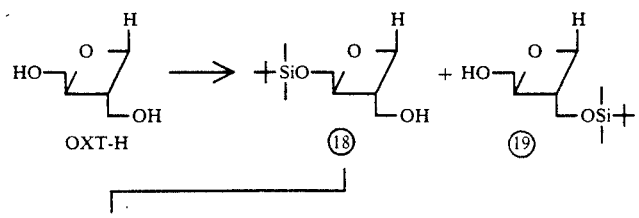

-continued

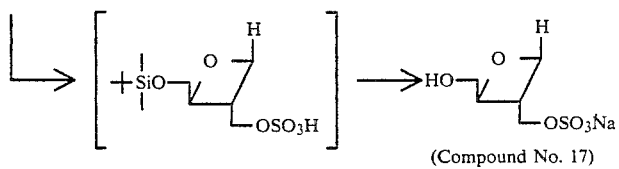

(Compound No. 17)

Under a stream of nitrogen gas, a solution of 337 mg of imidazole and 329 mg of t-butyldimethylsilyl chloride in 3.3 ml of anhydrous N,N-dimethylformamide is added to a solution of 500 mg of Oxetanocin-H in 9 ml of anhydrous N,N-dimethylformamide, and the resulting mixture is stirred at room temperature for 3 hour. After distilling off the solvent, the residue is diluted with 20 ml of water and extracted 8 times with each 20 ml portions of chloroform. The chloroform extract layer is washed with saturated aqueous solution of sodium chloride and dried over anhydrous sodium sulfate. After filtering off the sodium sulfate and distilling off the solvent, the residue is purified by silica gel column chromatography (50 ml, chloroform-methanol, 10:1). Then, the purified product is subjected to silica gel TLC (developing solvent: chloroform-methanol, 5:1), fractions having Rf value of about 0.49 are collected and the solvent is distilled off to obtain 212.7 mg (yield 29.3%) of Compound ⑱ as a colorless power. Further, fractions having Rf value of about 0.56 are collected to obtain 151.8 mg (yield 20.9%) of Compound ⑲ as a syrup.

Sulfur trioxide-pyridine complex (19.6 mg) is added to a solution of 30 mg of Compound ⑱ in 2 ml of N,N-dimethyl-formamide, and stirred at room temperature for 3 hours. Then, 100 microliters of 1.0M solution of tetrabutylammonium fluoride in tetrahydrofuran is added and stirred for 1.5 hours, after which the solvent is distilled off. The, 2 ml of water is added, and the mixture is passed through a 10 ml column of cation-exchange resin Dowex ® 50 W×8 (H³⁰) at 5° C. Fractions developing a color with sulfuric acid are collected and neutralized with 0.1N solution of sodium hydroxide. After distilling off the water, the residue is dissolved into ethanol containing 10% water and purified by column chromatography using 100 ml of Sephadex ® LH-20 previously equilibrated with the same solvent as above. Then, the purified product is subjected to silica gel TLC developing solvent n-butanol-water-acetic acid (4:2:1)], fractions having Rf value of about 0.16 are collected and the solvent is distilled off to obtain 5.3 mg (yield 52.7%) of Compound No. 17 as a colorless crystal.

Compound No. 17 : MS m/z; 355 (MH)⁺: NMR (200 MHz, D₂O) ppm: 8.50 (1H, s), 8.10 (1H, s), 6.47 (1H, d, J=6.0 Hz, 1'-H), 4.74 (1H, m, 3'-H), 4.23 (2H, m, 2'—CH₂), 3.94 (1H, m, 2'-H), 3.79 (2H, m, 3'—CH₂OH)

EXAMPLE 18

(Synthesis of Compound No. 18)

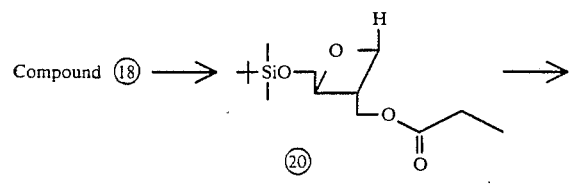

-continued

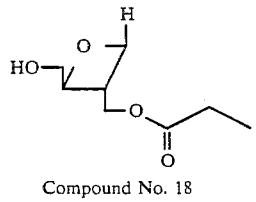

Compound No. 18

Under a stream of nitrogen gas, a catalytic quantity of 4-dimethylaminopyridine, 38 microliters of triethylamine and 14.2 microliters of propionyl chloride are added to a solution of 50 mg of Compound ⑱ in 4 ml of anhydrous chloroform, and the resulting mixture is stirred at room temperature for 2.5 hours. After distilling off the solvent, the residue is diluted with 10 ml of water and extracted thrice with each 10 ml portions of chloroform. The chloroform extract layer is washed with saturated aqueous solution of sodium chloride and dried over anhydrous sodium sulfate. After filtering off the sodium sulfate and distilling off the solvent, the residue is purified by silica gel column chromatography (20 ml, chloroform-methanol, 15:1). Then, the purified product is subjected to silica gel TLC (developing solvent: chloroform-methanol 10:1), fractions having Rf value of about 0.36 are collected and the solvent is distilled off therefrom to obtain 51.4 mg (yield 89.2%) of Compound ⑳ as a syrup.

Compound ⑳ : NMR (60 MHz, CDCl₃, TMS) ppm; 8.73 (1H, s), 8.46 (1H, s), 6.69 (1H, d, J=6.0 Hz, 1'-H), 4.89 (1H, m, 3'-H), 4.63 (2H, m, 2'—CH₂), 4.16 (3H, m, 2'-H, 3'—CH₂)( 2.63 (2H, q, J=7.0 Hz, MeCH₂CO), 1.43 (3H, near t, J=8.0 Hz, MeCH₂CO), 0.89 (9H, s, t-Bu), 0.13 (6H, s, SiMe)

To a solution of 51.4 mg of Compound ⑳ in 1 ml of anhydrous chloroform is added 145 microliters of 1.0M solution of tetrabutylammonium fluoride in tetrahydrofuran, and the resulting mixture is stirred at room temperature for 2 hours. After distilling off the solvent, the residue is dissolved into methanol containing 10% water and purified by silica gel column chromatography using 100 ml of Sephadex ® LH-20 previously equilibrated with the same solvent as above. Then, the purified product is subjected to silica gel TLC (developing solvent: chloroform-methanol, 5:1), fractions having Rf value of about 0.25 are collected and the solvent is distilled off therefrom to obtain 23.9 mg (yield 63.7%) of Compound No. 18 as a colorless power.

Compound No. 18: NMR (60 MHz, CD₃OD:CDCl₃=1:1, TMS) ppm: 8.65 (1H, s), 8.08 (1H, s), 6.53 (1H, d, J=6.0 Hz, 1'-H), 4.73 (1H, m, 3'-H), 4.47 (2H, m, 2'—CH₂), 3.37- 4.17 (3H, m, 2'-H, 3'—CH₂OH), 2.43 (2H, q, J=7.0 Hz, MeCH₂CO), 1.17 (near t, 3H, J=8.0 Hz, MeCH₂CO)

EXAMPLE 19

(Synthesis of Compound No. 19)

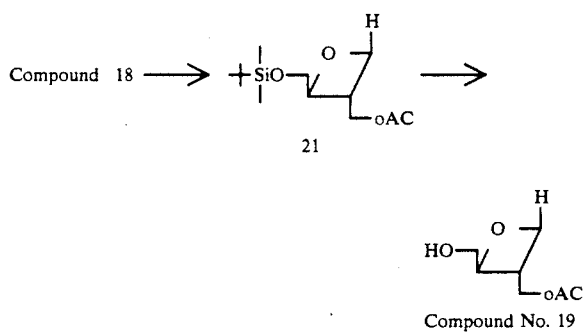

Compound No. 19

Under a stream of nitrogen gas, a catalytic quantity of 4-dimethylaminopyridine, 38 microliters of triethylamine and 16.8 microliters of acetic anhydride are added to a solution of 50 mg of Compound ⑱ in 4 ml of anhydrous chloroform, and the resulting mixture is stirred at room temperature overnight. Thereafter, in silica gel TLC (developing solvent: chloroform-methanol 10:1), fractions having Rf value of about 0.43 are collected and the solvent is distilled off in the same manner as in the case of Compound ⑳ to obtain 51.0 mg (yield 91.5%) of Compound ㉑ as a syrup.

Compound ㉑ : NMR (200 MHz, CDCl$_3$, TMS) ppm: 8.56 (1H, s), 8.23 (1H, s), 6.48 (1H, d, J=5.9 Hz, 1'-H), 4.63 (1H, m, 3'-H), 4.29 (2H, m, 2'—CH$_2$), 3.87 (2H, m, 3'—CH$_2$), 3.81 (1H, m, 2'-H), 2.12 (3H, s, AcO), 0.95 (9H, s, t-Bu), 0.17 (3H, s, SiMe), 0.15 (3H, s, SiMe).

To a solution of 28.1 mg of Compound ㉑ in 1 ml of anhydrous chloroform is added 200 microliters of 1.0M solution of tetrabutylammonium fluoride in tetrahydrofuran, and the resulting mixture is stirred at room temperature for 2 hours. Then, in silica gel TLC (developing solvent: chloroform-methanol 5:1), fractions having Rf value of about 0.23 are collected and the solvent is distilled off therefrom in the same manner as in the case of Compound No. 18 to obtain 12.8 mg (yield 63.3%) of Compound No. 19 as a colorless power.

Compound No. 19 : NMR (60 MHz, CD$_3$OD, TMS) ppm: 8.59 (1H, s), 8.02 (1H, s), 6.47 (1H, d, J=6.0 Hz, 1'-H), 4.70 (1H, m, 3'-H), 4.37 (2H, m, 2'—CH$_2$), 3.77–4.17 (3H, m, 2'-H, 3'—CH$_2$OH), 2.07 (3H, s, AcO)

EXAMPLE 20

(Synthesis of Compound No. 20)

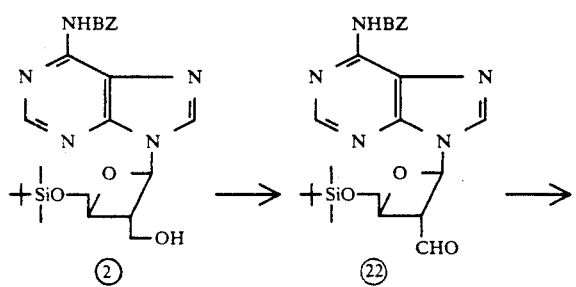

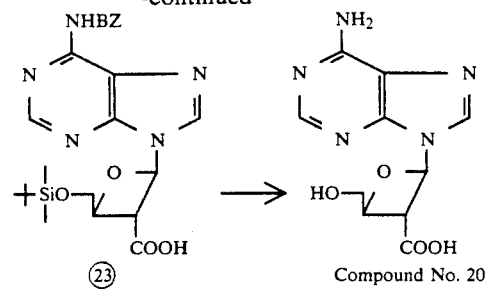

Compound No. 20

Under a stream of nitrogen gas, 18.2 microliters of dimethyl sulfoxide is added to a solution of 14.0 microliters of oxalyl chloride in 0.3 ml of anhydrous dichloromethane and the resulting mixture is stirred for 10 minutes at a temperature of −70° C. Then, a solution of 50 mg of Compound ② in 0.5 ml of anhydrous dichloromethane is dropwise added thereto, and the resulting mixture is stirred at −70° C. for one hour. Then 120 microliters of triethylamine is added and stirred for 5 minutes, after which it is diluted with 10 ml of water and thrice extracted with each 10 ml portions of chloroform. The chloroform extract layer is washed with saturated aqueous solution of sodium chloride and dried over anhydrous sodium sulfate. After filtering off the sodium sulfate and distilling off the solvent, the syrupy residue is purified by silica gel column chromatography (20 ml, chloroform-methanol, 20:1). Then, the purified product is subjected to silica gel TLC (developing solvent: chloroform-methanol, 20:1), fractions having Rf value of about 0.70 and developing a color with 2,4-dinitrophenylhdrazine are collected and the solvent is distilled off therefrom to obtain 43.1 mg (yield 86.3%) of Compound ㉒ as a syrup.

Compound ㉒ : MS m/z; 468 MH)$^{30}$ ; NMR (60 MHz, CD$_3$OD, TMS) ppm; 8.83 (1H, s), 8.63 (1H, s), , 7.23–8.17 (5H, m, ph), 6.61 (1H, d, J=6.0 Hz, 1'-H), 4.89 (1H, m, 3'-H), 3.50–4.03 (3H, m, 2'-H, 3'—CH$_2$), 0.93 (9H, s, t-Bu), 0.13 (6H, s, SiMe)

Ten drops of Jones reagent is added to a solution of 34 mg of Compound ㉒ in 3 ml of acetone, and the resulting mixture is stirred at room temperature for one hour. After distilling off the solvent, 10 ml of water is added to the residue, and it is thrice extracted with each 10 ml portions of chloroform. The chloroform extract layer is washed with saturated aqueous solution of sodium chloride and dried over anhydrous sodium sulfate. After filtering off the sodium sulfate and distilling off the solvent, the residue is purified by silica gel column chromatography (20 ml, chloroform-methanol, 2:1). Then, the parified product is subjected to silica gel TLC (developing solvent: chloroform-methanol, 5:1), fractions having Rf value of about 0.23 are collected and the solvent is distilled off therefrom to obtain 27.3 mg (yield 70.0%) of Compound ㉓ as a colorless powder.

Compound ㉓ : NMR (60 MHz, CD$_3$OD, TMS) ppm: 8.84 (1H, s), 8.67 (1H, s), 7.1–8.2 (5H, m, ph), 6.81 (1H, d, J=6.0 Hz, 1'-H), 4.80 (1H, m, 3'-H), 3.90–4.46 (3H, m, 2'-H, 3'—CH$_2$), 0.97 (9H, s, t-Bu), 0.13 (6H, s, SiMe)

To a solution of 17 mg of Compound ㉓ in 1 ml of tetrahydrofuran is added 0.3 ml of 0.1M solution of tetrabutylammonium fluoride in tetrahydrofuran, and the resulting mixture is stirred at room temperature for one hour. After distilling off the solvent, the residue is dissolved into 2 ml of methanol, 2 ml of concentrated ammonia water is added, and the resulting mixture is stirred at 60° C. for 1.5 hours. The syrupy product thus formed is dissolved into methanol containing 10% of water and purified by a column chromatography using 100 ml of Sephadex ® LH-20 previously equilibrated with the same solvent as above. Then, the purified product is subjected to silica gel TLC [developing solvent: n-butanol-water-acetic acid (4:2:1)], fractions having Rf value of about 0.43 are collected and the solvent is distilled off therefrom to obtain 2.9 mg (yield 31.2%) of Compound No. 20 as a colorless powder.

Compound No. 20: MS m/z; 266 (MH)+; NMR (400 MHz, CD₃OD, TMS) ppm: 8.61 (1H, s), 8.20 (1H, s), 6.66 (1H, d, J=6.6 Hz, 1'-H), 4.89 (1H, m, 3'-H), 4.41 (1H, m, 2'-H), 3.91 (2H, m, 3'—CH₂OH)

What is claimed is:

1. An oxetanocin-related compound represented by the following formula (I):

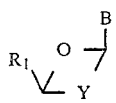
(I)

wherein R₁, Y and B have the following meanings;
R₁ represents —CH₂OH, and
(a) Y represents

and B represents

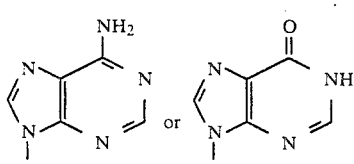

or
(b) Y represents

and B represents

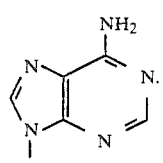

2. An oxetanocin-related compound according to claim 1, wherein Y represents

and B represents

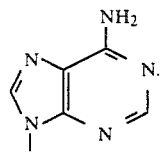

3. An oxetanocin-related compound according to claim 1, wherein Y represents

and B represents

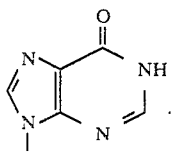

4. An oxetanocin-related compound according to claim 1, wherein Y represents

and B represents

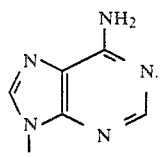

5. A pharmaceutical composition comprising in a pharmaceutically effective amount, an oxetanocin-related compound represented by the following formula (I):

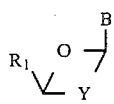
(I)

wherein R₁, Y and B have the following meanings:
R₁ represents —CH₂OH, and
(a) Y represents

and B represents

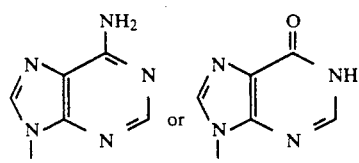 or
or
(b) Y represents
and B represents
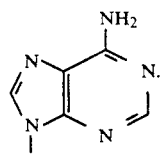
6. A pharmaceutical composition according to claim 5, wherein Y represents
and B represents
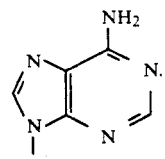
7. A pharmaceutical composition according to claim 5, wherein Y represents
and B represents
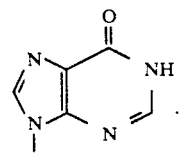
8. A pharmaceutical composition according to claim 5, wherein Y represents
and B represents
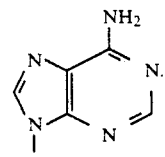
* * * * *